(12) United States Patent
Ricciardelli et al.

(10) Patent No.: US 11,963,757 B2
(45) Date of Patent: Apr. 23, 2024

(54) SIDE-STREAM RESPIRATORY GAS MONITORING SYSTEM

(71) Applicant: Treymed, Inc., Sussex, WI (US)

(72) Inventors: Robert H. Ricciardelli, Waukesha, WI (US); Michael J. Marking, Menomonee Falls, WI (US)

(73) Assignee: Treymed, Inc., Sussex, WI (US)

( * ) Notice: Subject to any disclaimer, the term of this patent is extended or adjusted under 35 U.S.C. 154(b) by 525 days.

(21) Appl. No.: 15/195,184

(22) Filed: Jun. 28, 2016

(65) Prior Publication Data

US 2017/0367618 A1    Dec. 28, 2017

(51) Int. Cl.
| | |
|---|---|
| *A61B 5/087* | (2006.01) |
| *A61B 5/00* | (2006.01) |
| *A61B 5/08* | (2006.01) |
| *A61B 5/097* | (2006.01) |

(52) U.S. Cl.
CPC ............ *A61B 5/087* (2013.01); *A61B 5/0022* (2013.01); *A61B 5/082* (2013.01); *A61B 5/097* (2013.01); *A61B 5/7203* (2013.01); *A61B 5/7246* (2013.01); *A61B 5/742* (2013.01)

(58) Field of Classification Search
CPC ................................ A61B 5/082; A61B 5/087
See application file for complete search history.

(56) References Cited

U.S. PATENT DOCUMENTS

| | | |
|---|---|---|
| 4,178,919 A | 12/1979 | Hall |
| 8,459,261 B2 | 6/2013 | Ricciardelli et al. |
| 2007/0107728 A1* | 5/2007 | Ricciardelli ........... A61B 5/087 128/204.21 |
| 2011/0161016 A1 | 6/2011 | Middendorp et al. |
| 2013/0006133 A1 | 1/2013 | Doyle et al. |

FOREIGN PATENT DOCUMENTS

EP    2301435 A1    3/2011

OTHER PUBLICATIONS

Supplemental European Search Report—date of completion Jan. 15, 2020.

* cited by examiner

*Primary Examiner* — Tse W Chen
*Assistant Examiner* — Michael A Catina
(74) *Attorney, Agent, or Firm* — Boyle Fredrickson, S.C.

(57) ABSTRACT

A side-stream respiration monitoring system that is configured to generate an alignment57, 59 signal and assess information that is derived in part from the alignment signal to align in a time domain the respiration flow and composition information. The system includes an analyzer that is fluidly connected to a flow sensor that is disposed in a respiration flow path. The system includes a controller that is configured to initiate delivery of the alignment signal to the flow sensor during a portion of at least one breath cycle. The controller is configured to determine a flow rate of respiration flow and at least a portion of a composition of the respiration flow on a breath-by-breath basis and temporally associate the respiration flow value and the determined portion(s) of the composition of the respiration flow as a function of information associated with the alignment signal generated by the analyzer.

20 Claims, 28 Drawing Sheets

SIDE-STREAM RESPIRATORY GAS MONITORING SYSTEM

FIELD OF THE INVENTION

The present invention relates to a system and method for monitoring respiration and, more particularly to a respiration monitoring system that is configured to monitor respiratory and physiological performance of a person being monitored. The invention provides a system and method for real time, breath-by-breath side-stream monitoring of a patient. The system monitors respiration flow rate and flow constituents to assess various parameters of a patient's physiological condition and respiration performance and is configured to effectuate temporal alignment of respiration flow and gas concentration data.

BACKGROUND OF THE INVENTION

As disclosed in Applicant's U.S. Pat. No. 8,459,261, it is generally well accepted that monitoring respiration performance provides diagnostic insight into a patient's overall health as well as specific respiratory function. Understandably, the accuracy of any diagnosis or conclusion based on respiratory performance depends upon the skill of the technician interpreting the interpretation as well, the accuracy of the information acquired, and the timeliness of the calculation of the information. Respiratory monitoring generally requires the acquisition of the breath sample and a determination of a make-up or composition of the acquired breath sample. Physiologic events, patient condition, equipment construction and operation, and ambient conditions directly affect the accuracy of the information acquired by the respiration monitoring system. Accordingly, failure to account for activities associates with these events detrimentally affects the accuracy of the information acquired and any conclusions based thereon. Furthermore, the timeliness of the respiration performance determination directly affects patient treatment determinations.

The cardiac cycle is one physiological event that can be taken, into account in generating respiratory performance information. During the cardiac cycle, expansion of the chambers of the heart compresses against the lungs and generates a flow anomaly in the respiration cycle. Although the flow anomaly is internally imperceptible to most people, the flow anomaly presents a discontinuity in the respiratory flow that, if unaddressed, can lead to inaccurate interpretation of respiration performance. Other physiological conditions, such as poor lung performance, can also detrimentally affect interpretation of monitored respiration information. Flow path dead-space is another factor that must be addressed to provide an accurate determination of respiration performance. The flow path dead-spaces include patient respiration dead-spaces as well as dead-spaces associated with respiration monitoring system, or aspiration dead-spaces.

Respiration flow path dead-spaces are those portions of a respiration path that are susceptible to retaining exhalation or inhalation gases. Within a patient, the tracheal passage, mouth, and tongue can each contribute to respiration flow dead-spaces. Gases from a previous inhalation or exhalation cycle may momentarily remain in these spaces even though a subsequent inhalation or exhalation has begun. Within the monitoring equipment, the connection lines and sensor construction can each present dead-space data collection errors. That is, the lines that connect the sensor to the monitor and the sensor inserted into the respiration flow path may each retain gases associated with a previous inhalation of exhalation cycle. The accuracy of any respiration monitoring depends in part upon the monitoring systems ability to correct the respiration performance information for each of these exemplary dead-spaces.

Ambient conditions also affect the accuracy of the information acquired during respiration monitoring. For example, in an oxygen rich environment, an exhalation that includes elevated levels of oxygen would not provide an accurate indication of respiration performance if compared to respiration performance for an environment that does not include the elevated levels of oxygen. Similarly, an exhalation that includes excessive amounts of carbon dioxide provides no indication of the physiological performance if the testing environment is already rich in carbon dioxide. Accordingly, accurate respiration monitoring system must also account for deviations in the ambient test conditions.

Capnography, or the measurement of carbon dioxide in an exhalation, is commonly performed in many medical fields, including ventilated patients. Knowing the concentration of carbon dioxide as a function of time renders information about breath frequency, e.g. breaths per minute, and inspired or re-breathed levels of carbon dioxide. In some circumstances there is good agreement between the highest levels measured, often the end-tidal concentration of the carbon dioxide, and an arterial concentration, which is of value in caring for seriously compromised individuals. Understandably, such methods of comparing exhaled carbon dioxide levels to arterial carbon dioxide levels lack real-time monitoring of respiration performance.

Ascertaining an actual amount of a chemical being consumed or generated by a patient enhances the temporal or real-time monitoring and diagnosis of a patient condition. That is, monitoring both the respiration composition as well as volume enhances the diagnostic feature of a respiration monitoring system. Prior methods have relied upon collecting the exhalation gases and analyzing them sometime after the exhalation to ascertain the condition of the patient. This method, commonly referred to as the "Douglas Bag" collection method, is cumbersome, labor intensive, and discounts all of the information that can be acquired with real-time breath-by-breath data acquisition and analysis. This method is also commonly referred to as 'indirect calorimetry' for its indirect determination of the caloric expenditure of a patient by quantifying the carbon dioxide produced. Accordingly, it is desired to provide a respiration monitoring system that is configured to directly measure gas volumes as they are being produced or in real-time and preferably on a breath-by-breath basis.

To accomplish the measuring of gas volumes on a breath-by-breath basis, the gas concentrations as a function of time must be collected simultaneously with the flow information. Gas concentrations measured at the same location and at the same time as the flow measurement are commonly referred to as mainstream monitoring. A disadvantage of mainstream monitoring is that the monitoring is commonly performed at the location of the patient's exhaled breath, i.e., the mouth, or as close to the site of exhalation as possible. The equipment commonly utilized for such monitoring generally tends to be large, cumbersome, and costly. Another drawback of such monitoring systems is the increase in dead-space volumes that must be overcome by a patient. Attempts at miniaturizing these devices only further increases the cost associated with these diagnostic tools. Accordingly, there is a need for a lightweight, portable respiration monitoring system with reduced dead-space volumes.

Although side-stream systems, also known as metabolic carts, address most of these issues, such systems present other drawbacks. A side-stream system draws a sample of the patient's breath and transmits it to a remote gas concentration analyzer. A side-stream system is normally capable of measuring the flow in real time. However, the acquired expiration sample must travel some distance thru lumen tubing or the like to reach the gas content analyzer. Since the gas sample is analyzed at some time after the passage of the patients flow, such side-stream systems present a temporal misalignment between the value of the respiration flow and the gas concentration values. This temporal or time wise misalignment makes side-stream systems more difficult to implement and the data acquired therefrom more difficult to interpret. Accordingly, technicians must be extensively trained in the operation and understanding of the information acquired with such systems. As such, there is also a need for a respiration monitoring system that is cost effective to manufacture, implement, and operate.

Another consideration of respiration monitoring systems is calibration of the monitoring system as well as the display of the acquired information. The calibration of known respiratory monitoring systems is a time consuming and labor intensive process. The calibration generally consists of a technician passing a known volume of a known gas several times into the monitoring system. The combination of the known gas and the relatively known volume provides operative information that provides for calibrating the monitoring system. Unfortunately, the calibration process is generally only performed at the initiation of a monitoring session, must be frequently repeated to ensure the accurate operation of the monitoring system, and does not adequately address variations in the testing environment. Additionally, such calibration generally relies heavily on the experience of the technician performing the calibration and the availability of the calibration tools such as a gas tube injector of a known volume and a known gas.

The output of known monitoring systems also presents the potential for misinterpretation. During inhalation, the monitored oxygen level should be at a maximum level and the monitored carbon dioxide level should be at a minimum, i.e. ambient conditions. During exhalation, the detected oxygen level should be at a minimum and the detected carbon dioxide level should be a maximum. The inverse relationship of the oxygen level and the carbon dioxide level across a respiration cycle as well as the dynamic function of the respiration flow is generally not temporary aligned across a respiration cycle. As shown in FIG. 1, the respiration information is generally produced with no cyclic alignment and a technician must mentally align the output to generate a real-time flow and composition of the respiratory function. FIG. 1 represents a trend plot 8 that includes a carbon dioxide trend 10 and a flow trend 12. A first ordinate 14 shows that the carbon dioxide trend 10 is always positive as indicated by abscissa 15 and ranges from a plurality of relative minimums 16 to a plurality of relative maximums 18. As discussed above, the relative maximums 18 of the carbon dioxide trend 10 reflect patient expiration whereas areas proximate relative minimums 16 reflect carbon dioxide levels associated with dead-space data acquisition and ambient carbon dioxide levels.

Flow trend 12 is indexed at second ordinate 20. Flow trend 12 repeatedly crosses abscissa 15 such that positive values indicate an inhalation and negative values indicate an exhalation. As discussed above, each exhalation, a flow associated with a negative flow trend value, should correlate to a relative maximum of the carbon dioxide trend. As indicated with the reference letters A, B, C, and D, temporally aligning the flow trend and the carbon dioxide trend requires phase shifting of flow trend 12 to the right relative to carbon dioxide trend 10. An identifier must be acquired to ensure an appropriate shift of the relative trends in determine the time-wise alignment of the flow and respiration composition information. Another lacking of known respiration monitoring systems is the ability to concurrently align a respiration flow value, a carbon dioxide concentration value, and an oxygen concentration value. Frequently, a carbon dioxide value and an oxygen value are displayed on different axis or completely different screens and therefore are not time aligned for interpretation.

Each of the drawbacks discussed above result in shortcomings in the implementation of known respiration monitoring systems. The cost and complexity of these respiration monitoring systems result in their infrequent utilization or improper interpretation of the results acquired with such systems. Furthermore, the information acquired and utilized by such systems limits the diagnostic functionality of such systems in disregarding that information that can be utilized by time aligning the variable functions of the respiration cycle and variations in operation of the monitoring system. Although Applicant's prior patent U.S. Pat. No. 8,459,261 resolved a number of considerations discussed above, improvements to the accuracy, ease of operation, and accuracy of the data collected and displayed by the respiration monitoring system disclosed therein are disclosed herein.

For instance, the respiration monitoring system disclosed in Applicant's U.S. Pat. No. 8,459,261 discloses a flow and composition data alignment methodology wherein patient physiologic events, such as cardiac cycle artifacts, can be ascertained from the acquired composition and flow data. However, the physiologic events associated with respiration monitoring of some patients may be insufficiently represented in the flow and composition data to achieve the desired degree of accuracy associated with the time-wise alignment of the flow and composition data. In an attempt to achieve time-wise alignment of the flow and composition data, others, such as the system disclosed in U.S. Patent Application 2011/0161016, disclose systems that mathematically manipulate the flow and/or composition data, or derivatives or integrands thereof, to manipulate the time-wise alignment of the acquired flow and composition data. Unfortunately, such approaches rely on the accuracy of the acquired data to effectuate the proposed time-wise alignment of the data.

Accordingly, there is a need for a real-time respiratory monitoring system that is configured to align respiration flow information and respiration composition information in a manner that relies on data acquired from the flow sensor and can be independent of a physiologic event associated with patient respiration performance. Furthermore, there is a need for a respiration monitoring system that is simple and efficient to manufacture and operate and one which provides concise real-time time aligned respiration performance information. There is a further need for respiration monitoring system capable of generating an alignment signal that can be acquired with the respiration flow and composition information and whose information can be used to verify and/or align in a time-domain the respiration flow and respiration flow composition information.

BRIEF DESCRIPTION OF THE INVENTION

The present invention is directed to a respiration monitoring system that overcomes one or more of the aforementioned drawbacks. A side-stream respiration monitoring system according to one aspect of the present invention includes an analyzer that is configured to be fluidly connected to a flow sensor that is constructed to be disposed in a respiration flow path. A controller is associated with the analyzer and is configured to initiate delivery of an alignment signal generated by the analyzer to the flow sensor during a portion of at least one breath cycle. The controller determines a respiration flow value and at least a portion of a composition of the respiration flow on a breath-by-breath basis and temporally associates in a time-domain the determined respiration flow value and the determined portion of the composition associated with the breath-by-breath basis as a function of information associated with the alignment signal delivered to the flow sensor by the analyzer during the portion of the at least one breath cycle. Such a system allows alignment or confirmation of the time-wise alignment of the respiration flow and respiration composition information during those instances when other data, such as data associated with respiration performance manipulating physiologic events, is unavailable or otherwise insufficient to establish the desired time-wise alignment of the acquired respiration flow and respiration composition information.

Another aspect of the invention discloses a method of monitoring patient respiration information. A patient respiration flow is measured and a side-stream breath sample is acquired via a flow sensor associated with a respiration flow path. The method includes generating an alignment signal and acquiring at least a portion of the alignment signal with the side-stream breath sample. A flow of the side-stream breath sample, a concentration of oxygen, and a concentration of carbon dioxide in the acquired side-stream breath sample are determined and aligned with one another in a time domain with respect to their occurrence in the acquired side-stream breath sample as a function of information associated with the portion of the alignment signal acquired with the side-stream breath sample.

Another aspect of the invention discloses a method of manipulating respiration performance data in a side-stream respiration monitoring system. The method includes introducing an alignment signal to a respiration flow passing through a sensor. A flow rate and at least a portion of a composition of a respiration flow passing through the sensor are determined and aligned with one another in a time domain from information attributable to the alignment signal.

Various other feature, aspects, and advantages of the present invention will be made apparent from the following detailed description and the drawings.

BRIEF DESCRIPTION OF THE DRAWINGS

The drawings illustrate one preferred embodiment presently contemplated for carrying out the invention. In the drawings.

DETAILED DESCRIPTION OF THE PREFERRED EMBODIMENT

Figure 2:
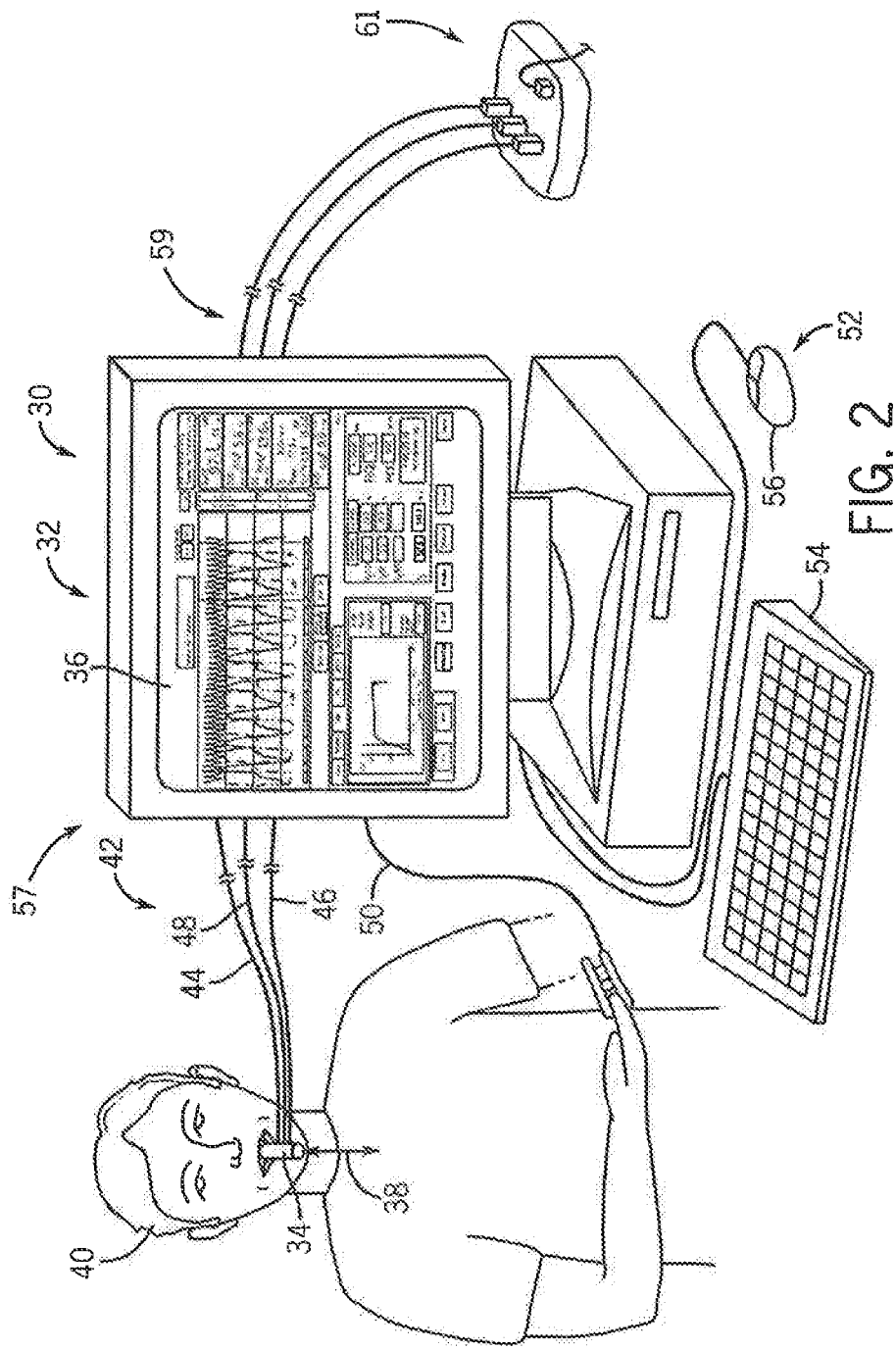
FIG. 2 is a perspective view of a side-stream respiration monitoring system according to the present invention.

FIG. 2 shows a monitoring system 30 according to the present invention. Monitoring system 30 includes a control or analyzer 32, a sensor 34, and a display 36. Sensor 34 is constructed to engage a respiration flow, indicated by arrow 38, or a participant or patient 40. A number of lumens or tubes 42 operatively connect sensor 34 to analyzer 32. A first and a second tube 44, 46 are connected to sensor 34 to detect a pressure differential of respiration flow 38 in sensor 34. A third tube 48 acquires an aspirated sample of respiration flow 38 and communicates the sample to analyzer 32. A physiological detector, preferably a heart rate monitor 50, is also connected to analyzer 32 and constructed to communicate a patient cardiac status to analyzer 32. Preferably, monitor 50 is configured to monitor both the pulsatile effects of the patient's cardiac cycle as well as the saturated oxygen content of the patient's circulation system.

Analyzer 32, having acquired the data or signals from tubes 42 and heart rate monitor 50, generates time aligned and composition corrected respiration information and outputs the information at display 36 as explained further below. Analyzer 32 includes optional user inputs 52 that allow a user to selectively configure the operation of analyzer 32 and the output of display 36 such that analyzer 32 and display 36 generate and output the desired information, respectively. It is further appreciated that display 36 can be constructed as a touch screen display such that a user or technician can manipulate the display results thereof and operation of analyzer 32 by touching selected areas of the display without utilization of auxiliary input devices such as a keyboard 54 and/or a mouse 56.

Figure 3:
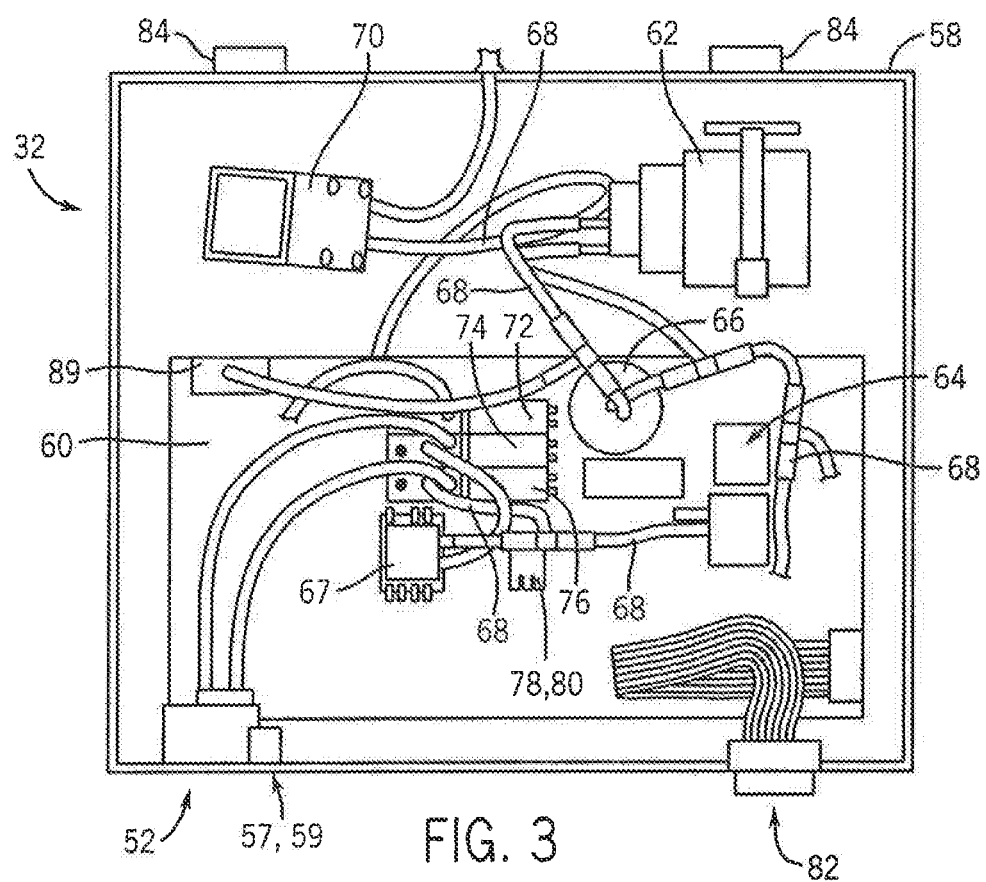
FIG. 3 is a plan view of an analyzer of the monitoring system shown in FIG. 2.

As described further with respect to FIG. 3, analyzer 32 includes a first input 57 and a second input 59 to allow multiple gas sources to concurrently be connected to analyzer 32. As shown in FIG. 2, first input 57 is connected to sensor 34 and second input 59 is connected to another sensor, a Douglas bag, gas cylinder, or container 61. It is appreciated that container 61 can be configured to contain a volume of a known gas or a volume of a gas collected from another patient. Such a configuration allows monitoring system 30 to monitor and assess multiple gas sources. Such a configuration is particularly useful in environments where monitoring of several patients is desired or where patients with reduced respiration tidal volumes, such as premature babies, have such low respiration volumes that collection of a respiration is required to assess the composition of the respiration gases.

Referring to FIG. 3, analyzer 32 includes a housing 58 having a control or controller 60 contained therein. An oxygen sensor 62, a nitrous oxide sensor 64, and a carbon dioxide sensor 66, and a flow sensor 67 are also positioned in housing 58. It is understood that oxygen sensor 62 be any of a number of technology based such as laser, acoustic, solid state, amperometric such as galvanic, or potentiometric. A number of tubes 68 interconnect sensors 62, 64, 66 and communicate respective portions of the acquired flow through the analyzer. A pump 70 and a number of valves 72, 74, 76 control the directional passage of the respiration flow through analyzer 32. Analyzer 32 includes a humidity sensor 78 and a temperature sensor 80 configured to monitor both ambient temperature and humidity as well as temperature and humidity of the respiration flow. It is further appreciated that analyzer 32 include an optional heater and/or humidifier to communicate thermal energy and/or moisture to a patient via the respiration flow.

Figure 4:
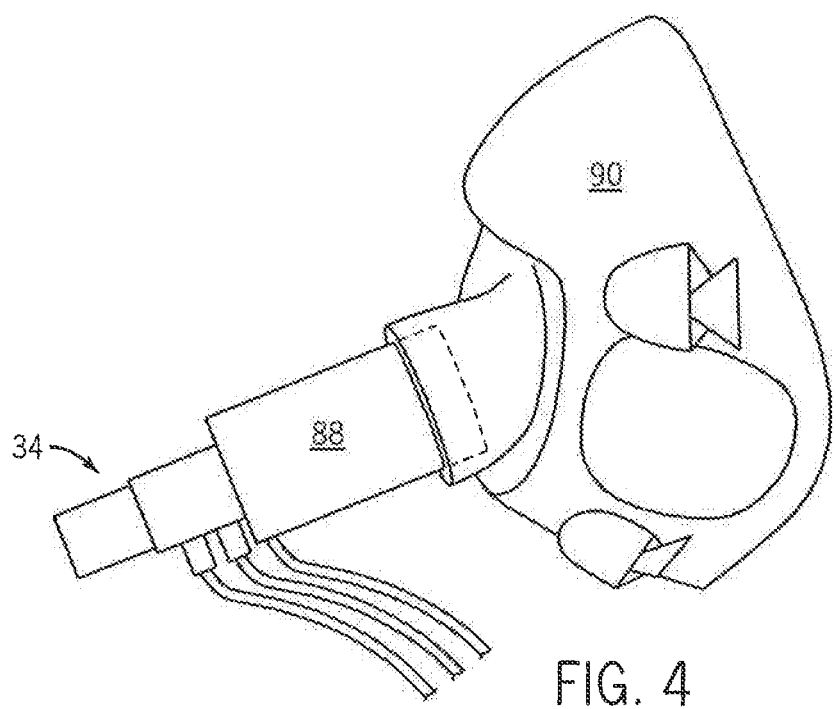
FIG. 4 is a perspective view of one embodiment of a sensor of the monitoring system shown in FIG. 1 with an optional adapter and mask attached to the sensor.

First input 57 and second input 59 extend through housing 58 and are constructed to removably engage the tubes 42 connected to sensor 34 or container 61 as shown in FIG. 2. An electrical connector 84 also extends through housing 58 and is constructed to communicate information generated by analyzer 32 to external devices such as personal computers, personal data assists (PDA's), cell phones, or the like. Alternatively, it is further understood that analyzer 32 include a wireless interface to allow wireless communication of the information acquired and calculated by analyzer 32 to external devices. Analyzer 32 includes an input connector 82 constructed to communicate information from patient monitor 50 to the analyzer. Input 84 is constructed to removably connect monitor 50 to analyzer 32 to communicate the information acquired by monitor 50 to the analyzer 32. It is understood that inputs and connectors 84 be any conventional connection protocol such as serial pin connectors, USB connectors, or the like, or have a unique configuration. Analyzer 32 further includes a leak test valve 89, the operation of which is described below with respect to the automatic calibration and performance monitoring of analyzer 32. It is appreciated that the relatively compact and lightweight nature of analyzer 32 provides a respiration monitoring system 10 that is highly portable and operable with a number of sensors. FIGS. 4-6 show a number of sensors that are applicable with the present invention.

FIG. 4 is an enlarged view of sensor 34 with an optional adapter 88 and an optional mask 90 connected thereto. Mask 90 ensures that nasal respiration is prevented or directed toward sensor 34 during a respiration monitoring procedure. Such a configuration ensures information indicative of an entire respiration flow is communicated to analyzer 32. Comparatively, adapter 88 is constructed to allow a portion of a respiration flow to bypass sensor 34. Such a configuration is particularly applicable to acquiring respiration data during periods of high respiration flow such as during adult or athlete stress testing procedures.

Figure 5A:
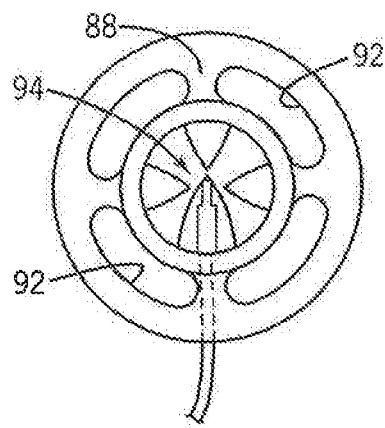
FIGS. 5a and 5b are elevational end views of the sensor shown in FIG. 4 with adapter connected to the sensor and the mask removed therefrom.
Figure 5B:
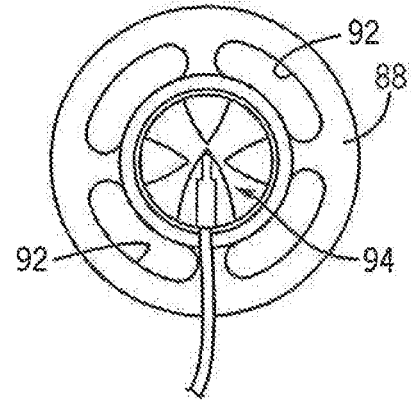

As shown in FIGS. 5a and 5b, adapter 88 includes a number of passages 92 constructed to allow a portion of a total respiration flow to pass to atmosphere thereby bypassing a flow passage 94 of sensor 34. Preferably, adapter passages 92 are configured to allow a flow that is a multiple of the flow directed through sensor 34 to pass through adapter 88. More preferably, passages 92 are constructed to allow a multiple of ten of the respiration flow directed through sensor 34 to pass through adapter 88. Such a configuration simplifies the calculation associated with determining the total flow information when only a fraction of the total flow is directed through the sensor 34. Adapter 88 facilitates the increased respiration flow generally associated with a stress test without overly burdening the respiration system of the patient or participant associated with requiring the entirety of the respiration flow to pass through the more constricted passage of sensor 34.

Figure 6A:
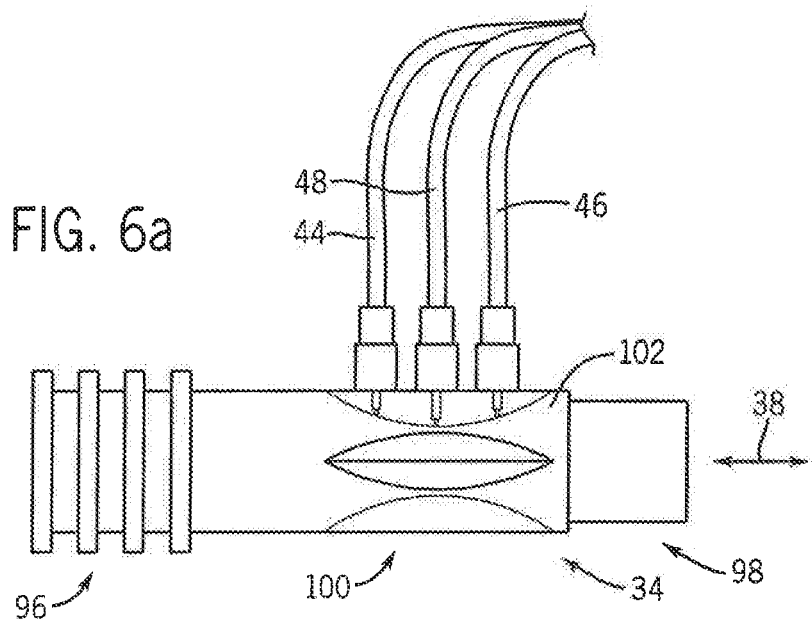
FIG. 6a is an elevational view of the sensor of the monitoring system shown in FIG. 5 with the adapter removed from the sensor.

FIG. 6a is a detailed view of sensor 34 with adapter 88 and mask 90 removed therefrom. Adapter 88 includes a patient end 96 and an atmosphere end 98. A sensor section 100 is generally disposed between the patient end 96 and the atmosphere end 98. Sensor section 100 includes a venturi-like section 102 constructed to generate a pressure differential between respective ends of the sensor section 100. Signals communicated to analyzer 32 via first tube 44 and second tube 46 allow analyzer 32 to detect the pressure differential across sensor section 100 and thereby provide information utilized to calculate the respiration flow 38 communicated through sensor 34. Third tube 48 acquires a sample of the respiration flow, or an aspiration, and communicates the acquired sample to the analyzer 32 which then determines the make-up or composition of the gas of the respiration flow. It is appreciated that the construction of the sensor may vary depending, in part, on a patient's respiration ability. That is, sensor 34 may be adapted to accommodate respiration monitoring of patients with low respiration tidal volumes or flows such as for analyzing respiration compositions associated with premature infants, neonatal patients or the like. For such applications sensor 34 may be configured to operate at a flow resistance over a differential pressure range of approximately 0-16 cm water which covers a smaller flow range generally in the range of 0 to ten liters per minute. Further details of the construction and operation of sensor 34 are disclosed in Applicant's U.S. Pat. Nos. 5,925,831 and D413,825 and U.S. Publication No. 2004/0254491, all of which are incorporated herein by reference.

Figure 6B:
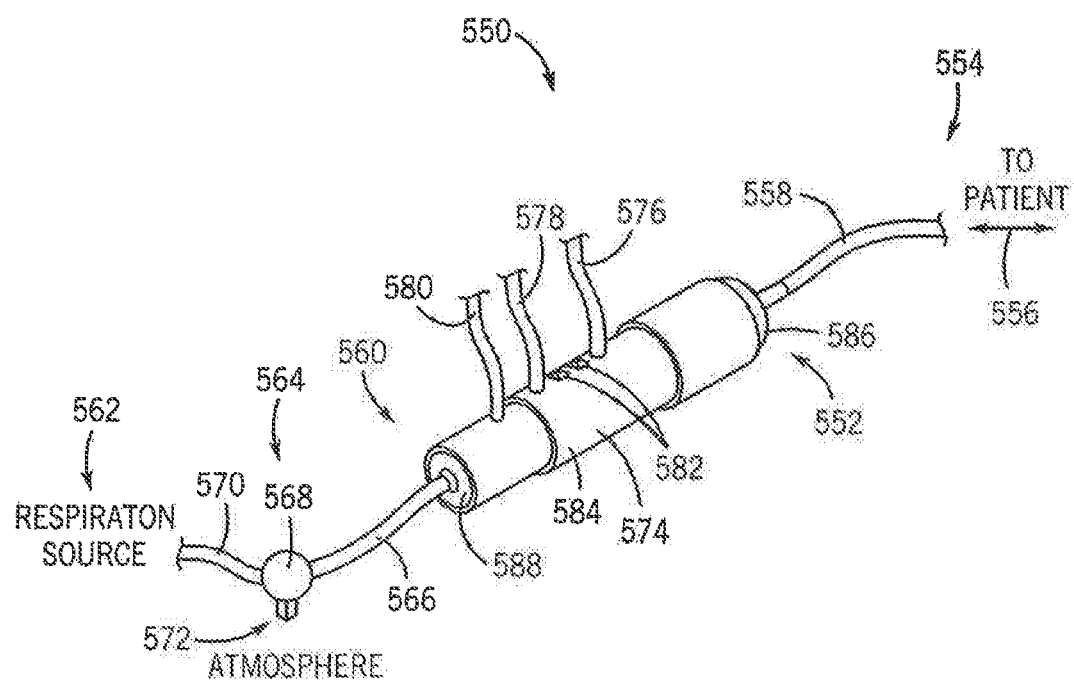
FIG. 6b is a perspective view of another sensor for use with the monitoring system shown in FIG. 5.

FIG. 6b shows another sensor 550 according to the present invention. A first end 552 of sensor 550 is constructed to be directed toward a patient side 554 of a respiration path, indicated by arrow 556. Sensor 550 includes an intubation tube 558 for those patients that are required to be intubated. Another end 560 of sensor 550 is constructed to be directed toward a source of respiration gas 562. For those patients that require respiration assistance, sensor 550 is connected to a respirator (not shown) by a tube assembly 564. Tube assembly 564 includes a first tube 566 constructed to extend between a valve 568 an end 560 of sensor 550. A second tube 570 extends between valve 568 and the respirator. Valve 568 includes a vent 572 and is constructed to direct an exhaled gas to atmosphere. Valve 568 is commonly understood as a "Wye" valve and is configured to prevent the direction of the exhalation toward the respirator. Understandably, gas directed through vent 572, rather than being dumped to atmosphere, could be connected to another tube and collected at a Douglas bag as described herein for analysis by analyzer 32.

Sensor 550 includes a body 574 that extends between first end 552 and second end 560. A number of tubes 576, 578, 580 are connected to body 574 and fluidly connected between the respiration path 556 and an analyzer 32. Tubes 576 and 578 are connected to sensor 550 and analyzer 32 to detect the flow associated with respiration path 556. Tube 580 is connected to sensor 550 to acquire an aspiration sample of the respiration gas. Unlike sensor 34, the aspiration sample acquiring tube 580 is positioned outside the space between the flow sensing tubes 576, 578. The importance of this distinction is described further below with respect to FIG. 6c. A number of cavities 582 are formed in an exterior surface 584 of body 574 and do not extend through the body 574 into the respiration path 556 formed therethrough. A first adapter 586 and a second adapter 588 are engaged with body 574 proximate first end 552 and second end 560, respectively. Adapters 586, 588 are configured to facilitate the connection of sensor 550 to tubes 558, 566 without detrimentally affecting the dead-space associated with sensor 550 or the patient dead-spaces discussed herein.

Figure 6C:
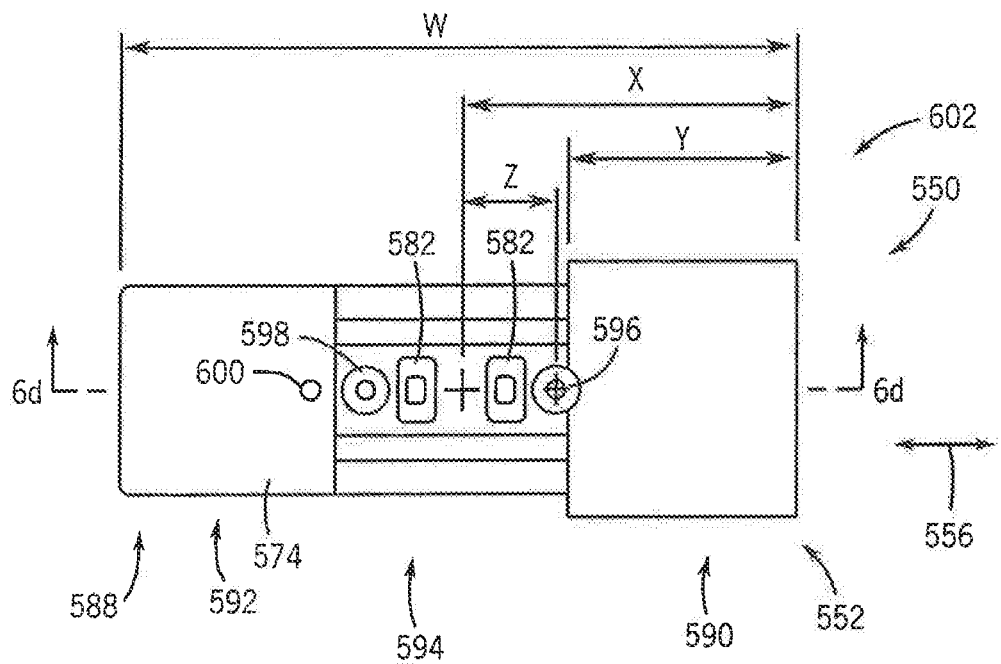
FIG. 6c is a plan view of the sensor shown in FIG. 6b.

FIG. 6c shows sensor 550 with adapters 586 and 588 removed therefrom. Body 574 includes a first section 590 constructed to removably engage adapter 586 and a second section 592 constructed to removably engage adapter 588. Understandably, adapters 586, 588 could be integrally formed with body 574 to provide a patient and application specific sensor 550. A detecting section 594 includes a first port 596 and a second port 598 fluidly connected to respiration path 556 with cavities 582 disposed between the ports 596, 598. Body 574 includes a sample port 600 that also extends through body 574 and is fluidly connected to respiration path 556. Sample port 600 extends through body 574 downstream from a patient side of respiration path 556 relative to first and second ports 596, 598. FIG. 6c also includes several exemplary dimension values 602 which show an exemplary positioning of ports 596, 598, 600 relative to first, second, and detecting sections 590, 592, 594 of body 574. Understandably, these dimensions are merely exemplary and other relative sizes and orientations are envisioned and within the scope of the claims.

Figure 6D:
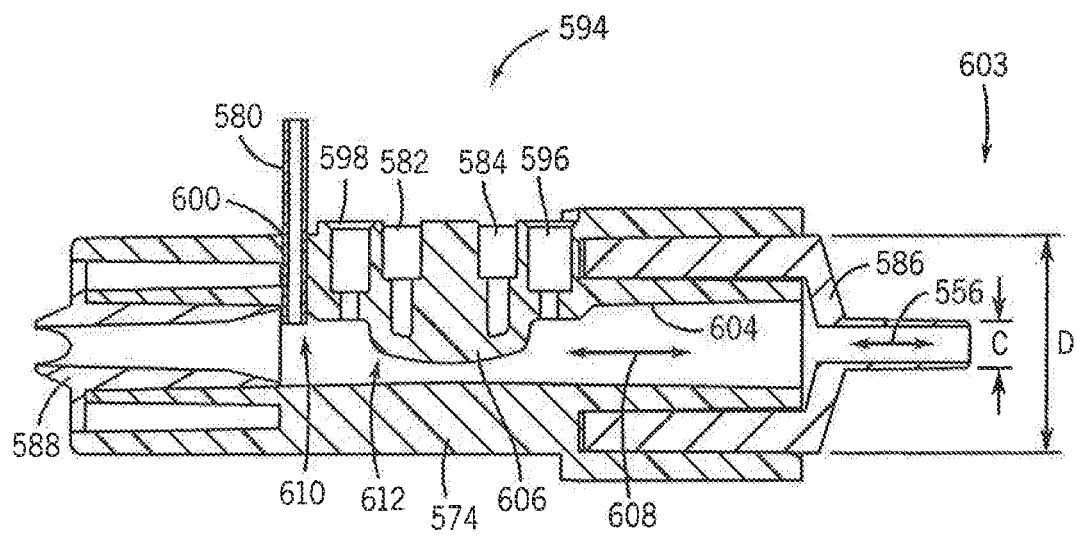
FIG. 6d is a cross-sectional view of the sensor shown in FIG. 6b along line 6d-6d.

FIG. 6d shows a cross-section of sensor 550 along line 6d-6d indicated in FIG. 6c with adapters 586, 588 connected thereto. FIG. 6d also includes several exemplary dimensions 603 associated with the relative size and construction of sensor 550. As shown in FIG. 6d, an interior surface 604 of body 574 includes a restricting member 606 that projects from interior surface 604 into a flow passage 608 of body 574. Preferably, restricting member 606 extends into flow passage 608 past the centerline of the passage 608 to create a pressure differential between ports 596, 598. In a preferred embodiment, restricting member 606 has a generally arcuate or curved outer surface. This pressure differential is communicated to analyzer 32 via ports 596, 598 and tubes 576, 578 (as shown in FIG. 6b) and is utilized to generate the respiration flow data. Cavities 582 extend into body 574 are prevent deformation of restricting member 606 from a desired shape and size during the forming process. Understandably, although two cavities 583 are shown, other numbers of cavities or cavity constructions are envisioned and within the scope of the claims.

Sample acquiring tube 580 is sealingly received in port 600 and has an end 610 that preferably extends beyond interior surface 604 of body 574 into flow passage 608. The extension of end 610 beyond the interior surface 604 of body 574 reduces the potential of collecting moisture associated with the respiration flow 556. Understandably, port 600 of body 574 could be constructed to include a nipple that would extend from interior surface 604 to provide this reduction in the potential collection of respiration condensation or water content. Tube 580 communicates the acquired sample to analyzer 32, or a Douglas bag, for a determination of the composition of the respiration gas.

The relative positioning of sample port 600 outside of the space between ports 596 and 598 is particularly applicable for respiration flow monitoring of those patients with reduced respiration flow tidal volumes such as premature infants. Generally, premature babies has such fast respiration rates with such low respiration tidal volumes that acquiring a respiration sample proximate restricting member 606 can detrimentally affect patient respiration. That is, acquiring a sample much closer to the patient than a trailing edge 612 of restricting member 606 has the effect of acquiring a sample that is larger than an actually expired sample. Accordingly, such a configuration has the effect of extracting respiration gas from a patient rather than allowing the patients anatomy to exhale the respiration gases. As such, sensor 550 is configured to allow breath-by-breath monitoring in even the smallest of patients. It is further appreciated that an interior surface, or respiration flow facing surface of one of more of sensors 34, 550 can include a hydrophobic or more preferably a hydrophilic layer or coating configured to effect the generation of condensate associated with the passage of the respiration flow through sensor 34 and to mitigate interference of condensate or moisture associated with the respiration flow with the acquisition of the flow and flow composition signals.

Figure 7A:
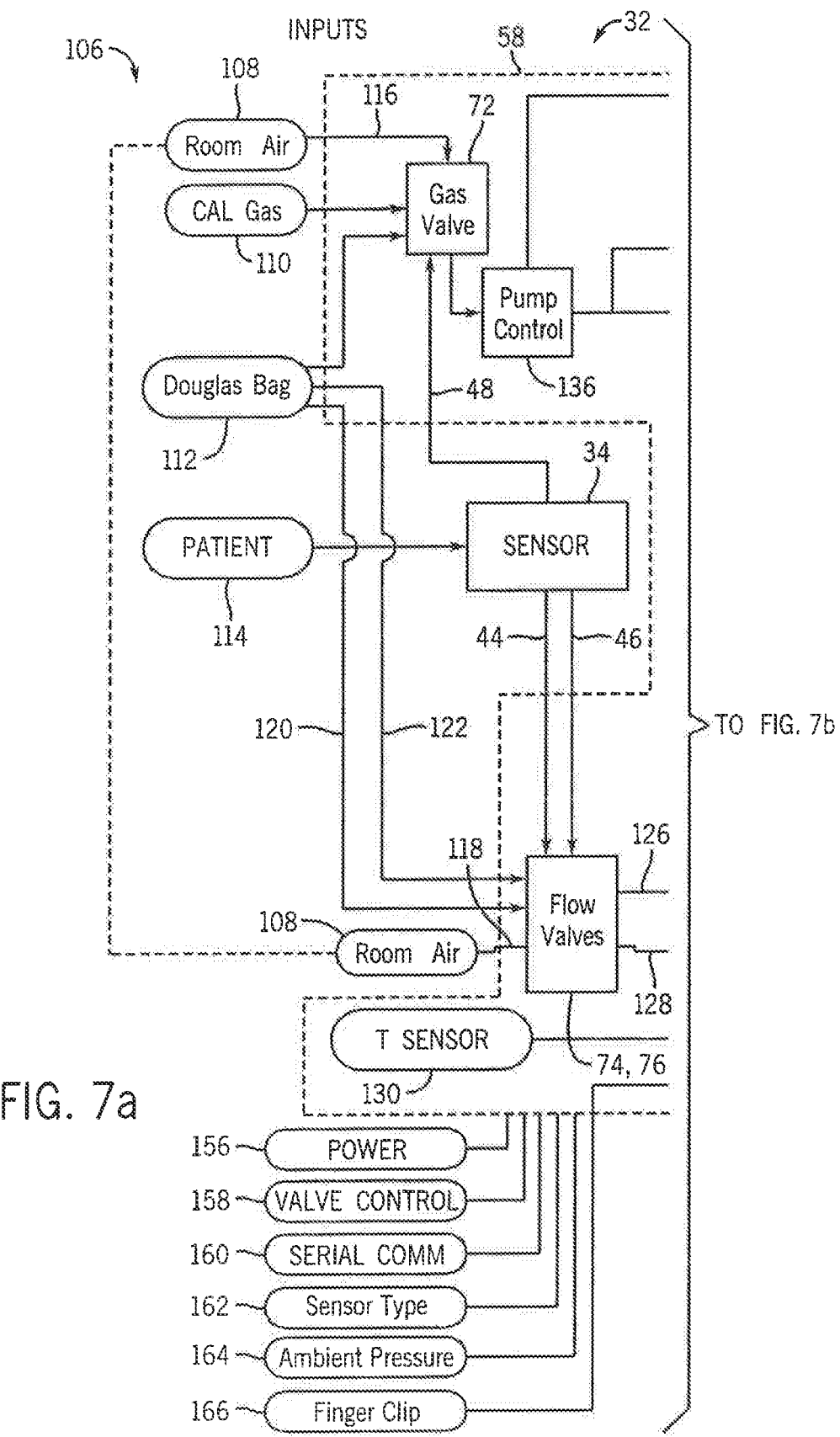
FIGS. 7a and 7b are a schematic representation of the monitoring system shown in FIG. 2.
Figure 7B:
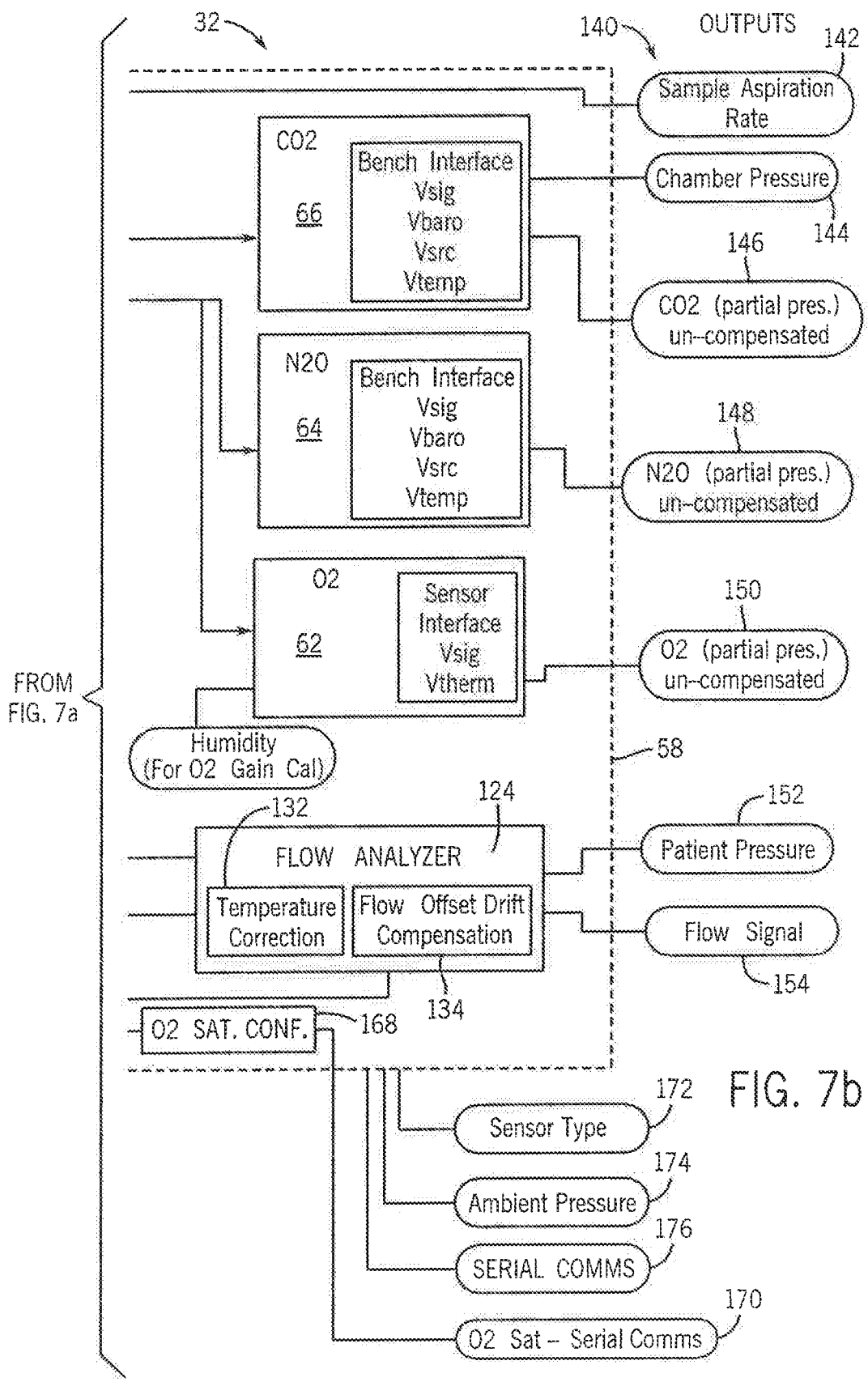

FIG. 7 shows a schematic representation of sample flow through analyzer 32. Analyzer 32 is constructed to receive any of a number of inputs 106 associated with a gas to be analyzed. Inputs 106 can include a room air or ambient input 108, a calibration gas input 110, a Douglas bag input 112, and a patient input 114. A first tube 116 communicates ambient input 108 to gas valve 72 and a second tube 118 communicates ambient input 108 to flow valves 74, 76 of analyzer 32. Similarly, tubes 44 and 46 connected to sensor 34 communicate patient flow-to-flow valve 74 and 76. When a Douglas bag input 112 is utilized with analyzer 32, a first tube 120 and a second tube 122 communicate a Douglas bag gas material to valves 74, 76. Understandably, it is appreciated that a Douglas bag is a container configured to store a respiration sample or a known expiration sample.

Regardless of the source of the input gas, flow valves 74, 76 communicate the received flow to a flow analyzer 124 via tubes 126, 128. Flow analyzer 124 is connected to a temperature sensor 130 and includes a temperature correction protocol 132 configured to detect and associate a detected flow with a respective temperature of the analyzer 32 or atmosphere. Temperature correction protocol 132 corrects the calculated flow value for variable temperatures associated with the test environment. Flow analyzer 124 includes a flow offset drift compensator 134 figured to account for drift variations associated with extended operation of analyzer 32. Accordingly, flow analyzer 124 is configured to adjust the measured flow parameter for variations associated with ambient conditions as well as operational variation of the flow analyzer 124.

Gas samples that are communicated to gas valve 72 are communicated to a pump control 136 and therefrom to each of oxygen sensor 62, nitrous oxide sensor 64, and carbon dioxide sensor 66. Oxygen sensor 62, nitrous oxide sensor 64, and carbon dioxide sensor 66 are configured to indicate the respective levels of the constituent gases contained in the input flow regardless of the source of the input gas. Accordingly, analyzer 32 is operable with a number of gas sources that can be concurrently connected to the analyzer 32. As will be described further, controller 60 is configured to assess which type of gas source is connected to the analyzer and initiate a monitoring sequence or a calibration sequence.

Still referring to FIG. 7, analyzer 32 generates a number of outputs 140, including a sample aspiration rate 142 that is derived from pump control 136. A chamber pressure value 144 and an uncompensated carbon dioxide value 146 are derived from carbon dioxide sensor 66. An uncompensated nitrous oxide value 148 is derived from nitrous oxide sensor 64 and an uncompensated oxygen value 150 is generated from oxygen sensor 62. Flow analyzer 124 generates patient pressure data 152 and respiration flow data 154. Analyzer 32 also includes a plurality of user inputs that include a power input 156, a valve control input 158, a serial communication input 160, a sensor-type selection 162, an ambient pressure input 164 and a patient finger clip 166 configured to monitor patient cardiac condition.

Analyzer 32 includes an oxygen saturation controller 168 that determines a patient oxygen saturation level communicated to the oxygen saturation controller 168 from an oxygen saturation serial communication link 170 constructed to engage the patient monitor 50. Analyzer 32 is also configured to generate an output associated with a sensor type 172 and an ambient pressure determination 174. As discussed above, analyzer 32 includes a number of serial communication links 176 that facilitate connectivity between analyzer 32 and other auxiliary devices such as personal computers, PDA's and the like. Such a configuration allows analyzer 32 to operate with a number of different flow input sources, be configured to operate with a number of gas and flow sensors, and provide a number of variable format outputs. Analyzer 32 is constructed to be dynamically responsive to the gases communicated to the analyzer, the connectivity modalities associated with the separable components of the monitoring system, and providing data that is in a user desired format.

Figure 8:
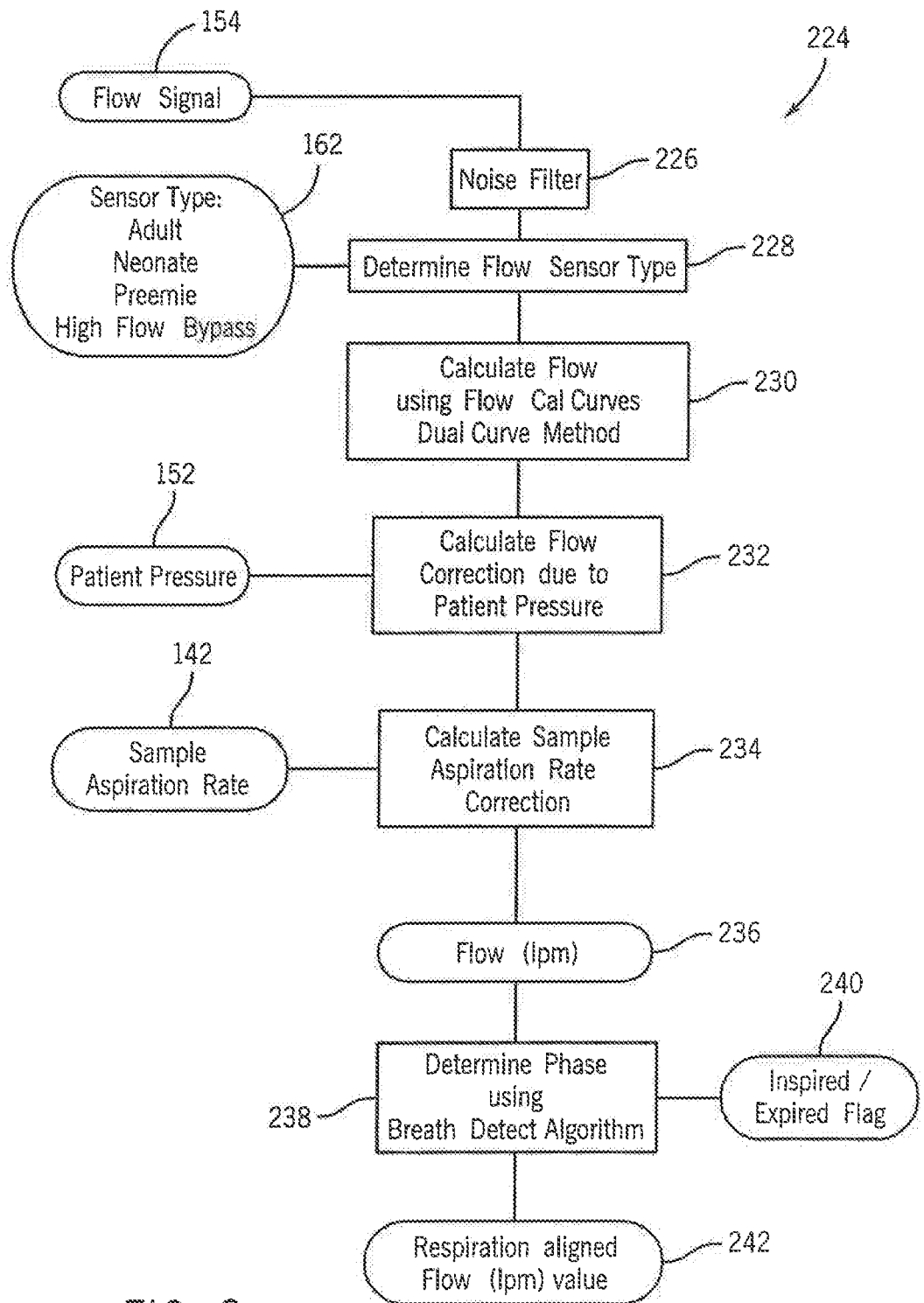
FIG. 8 is a schematic representation of a flow determination correction procedure performed by the monitoring system shown in FIG. 2

Analyzer 32 includes a flow determination and correction protocol 224 as shown in FIG. 8. Correction protocol 224 acquires respiration flow data 154 from flow analyzer 124 as shown in FIG. 7. A noise filter 226 addresses electrical signal noise associated with operation of flow analyzer 124. Correction protocol 224 is also configured to determine a sensor type 228 associated with acquisition of the flow. That is, the determination of the flow sensor type 228 determines whether the sensor is constructed to receive the respiration flow of an adult, a neonatal or infant, a premature baby, or a high-flow, i.e., bypass sensor configuration as previously described with respect to FIGS. 2-7.

Correction protocol 224 calculates the respiration flow 230 using a flow calculation curve as described below. A patient pressure flow correction 232 is calculated from the patient pressure data 152 as determined by flow analyzer 124. A sample aspiration rate correction 234, is implemented and utilizes the sample aspiration rate 142 generated from pump control 136 as shown in FIG. 7. Having calculated and corrected the flow based on patient pressure and aspiration rate correction, correction protocol 224 determines a respiration flow value 236 associated with each breath cycle of a monitored respiration cycle. The flow value 236 is then temporally aligned with a respiration phase 238 using an inspired/expired flag 240 as acquired from the respiration cycle. Having determined the phase of the associated flow value, correction protocol 224 generates a respiration aligned flow value 242 indicative of the flow value at any given time during a respiration cycle.

Figure 9:
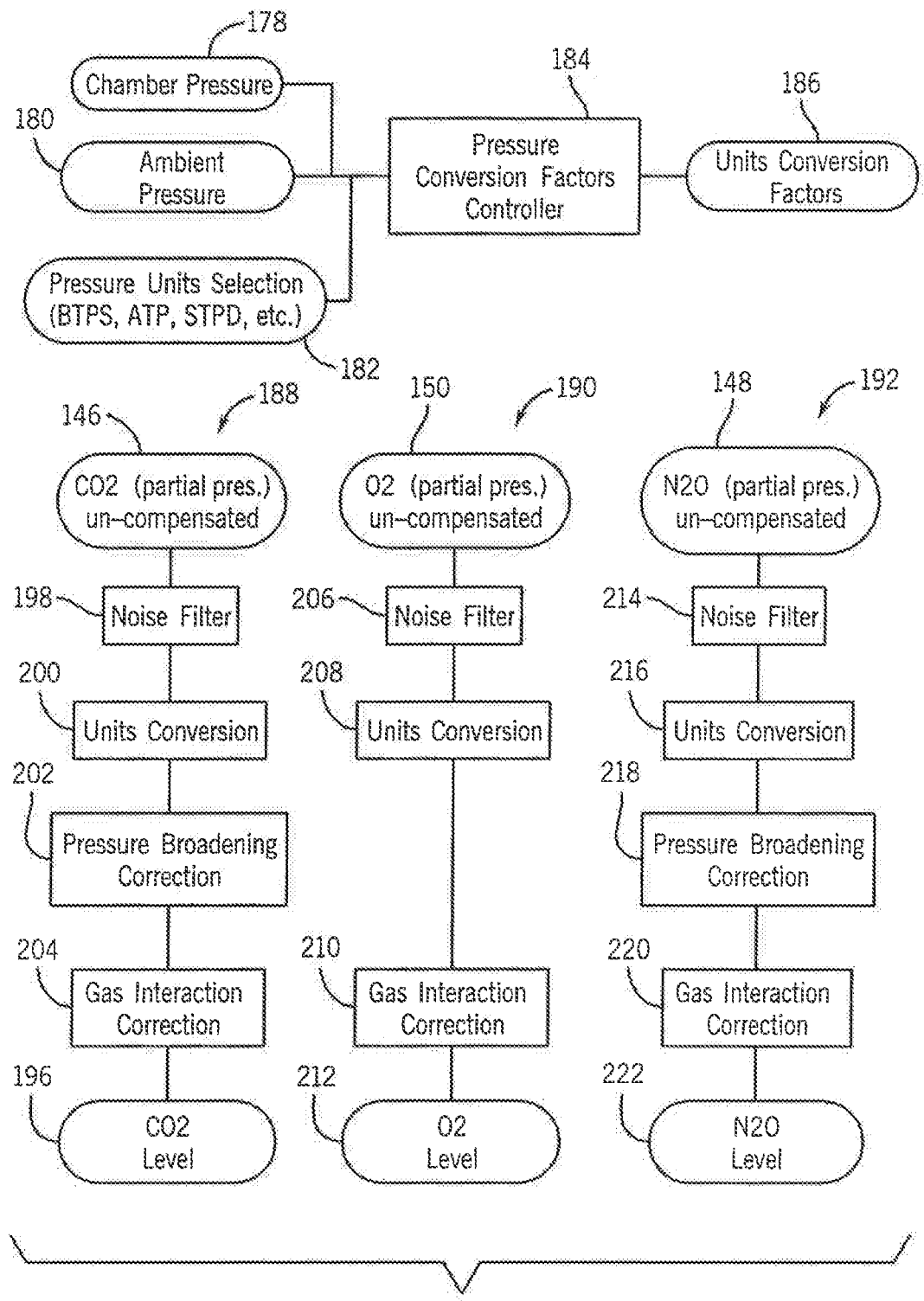
FIG. 9 is a schematic representation of a series of first composition correction operations performed by the monitoring system shown in FIG. 2.

FIG. 9 shows a number of first data correction procedures performed by analyzer 32. As discussed above with respect to FIG. 7, analyzer 32 is constructed to detect a chamber pressure 178, an ambient pressure 180, and is responsive to a pressure units selection 182. These parameters are input to a pressure conversion factor controller 184 that is configured to output a corrected detected pressure in desired units 186. Analyzer 32 also includes a carbon dioxide correction protocol 188, an oxygen correction protocol 190, and a nitrous oxide correction protocol 192. Carbon dioxide correction protocol 188 adjusts a respiration carbon dioxide value 194 by passing the uncompensated carbon dioxide value 146 through a noise filter 198, a unit converter 200, a pressure-broadening correction 202 and a gas interaction correction 204. Noise filter 198 is constructed to resolve electrical noise associated with operation of the carbon dioxide sensor 66. Unit converter 200 is constructed to convert the carbon dioxide value to user-desired units. Pressure broadening correction 202 is constructed to further adjust the uncompensated carbon dioxide value 146 with respect to operation of the carbon dioxide sensor 66 at the system, environment, or ambient operating pressure.

Gas interaction correction 204 corrects the uncompensated carbon dioxide value 146 for misrecognition of other gas molecules as carbon dioxide molecules. That is, due the nature of the operation of the carbon dioxide sensor 66, nitrous oxide molecules may occasionally be recognized by carbon dioxide sensor 66 as carbon dioxide molecules. Gas interaction correction 204 adjusts the uncompensated carbon dioxide value 146 for such occurrences to provide a carbon dioxide level 196 that is adjusted for these molecule misrecognition events.

Oxygen correction protocol 190 also includes a noise filter 206 configured to correct the uncompensated oxygen value 150 generated or provided by oxygen sensor 62. Noise filter 206 addresses the electrical noise associated with operation of oxygen sensor 62. A unit's conversion 208 is configured to provide an oxygen value associated with a desired user oxygen value units. Similar to gas interaction correction 204, oxygen correction protocol 190 includes a gas interaction correction 210 configured to correct the uncompensated oxygen value 150 for occurrences of oxygen sensor 62 interpreting non-oxygen molecules as oxygen. Oxygen correction protocol 190 generates an oxygen level value 212 that has been corrected for electrical noise associated with operation of the sensor 62. Similar to carbon dioxide correction protocol 188, nitrous oxide correction protocol 192 corrects an uncompensated nitrous oxide value 148 through utilization of a noise filter 214, a unit's conversion 216, pressure broadening correction 218 and a gas interaction correction 220 to provide a nitrous oxide level value 222 that more accurately reflects an actual amount of nitrous oxide contained in a respiration or gas sample and a value that has been corrected for the background noise associated with operation of the nitrous oxide sensor 64 and is in a user desired units. The nitrous oxide value has also been corrected for atmospheric and operational pressure differentials, and non-nitrous oxide gas interaction correction.

Figure 10:
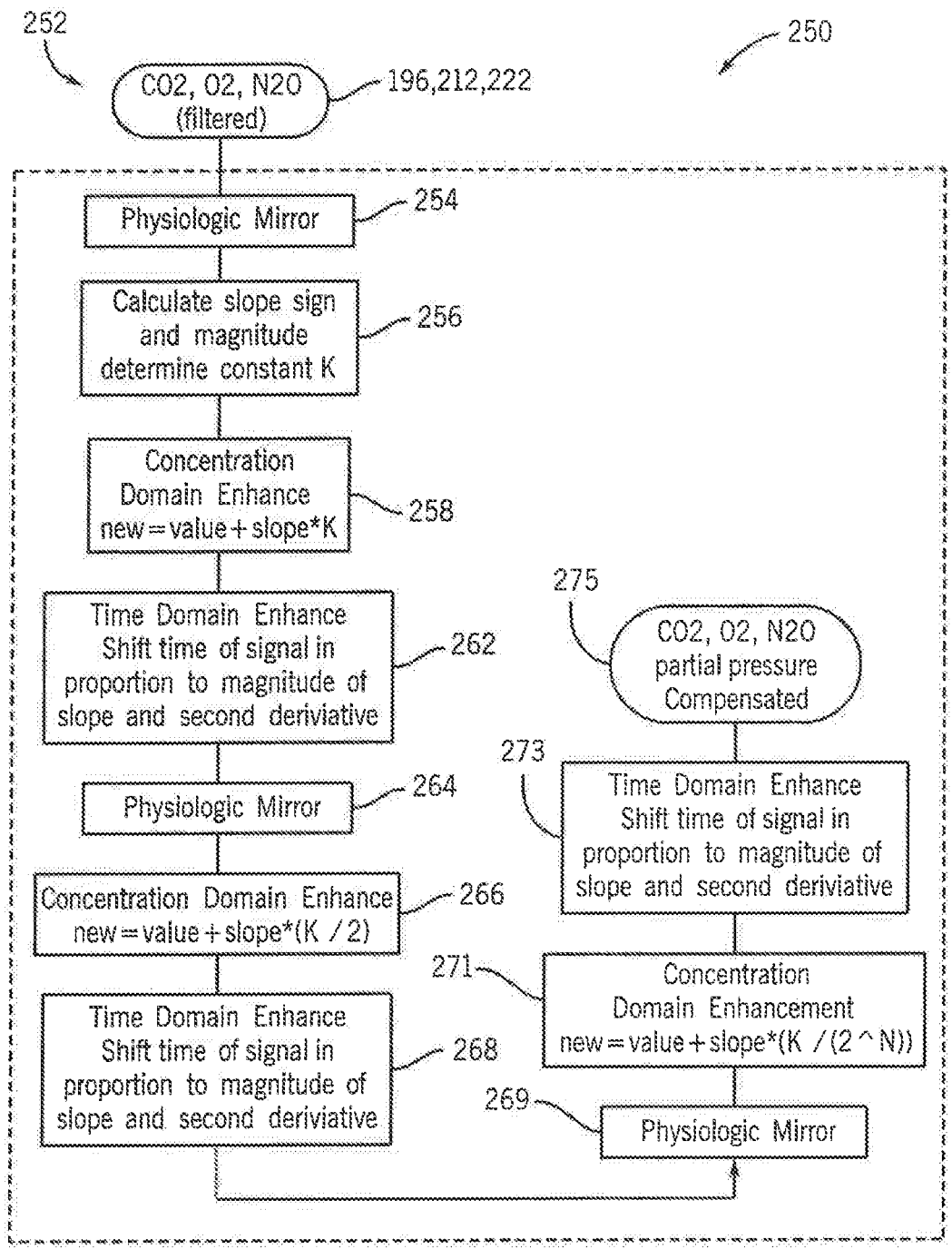
FIG. 10 is a schematic representation of a second composition correction procedure performed by the monitoring system shown in FIG. 2.

FIG. 10 shows a response time and enhancement protocol 250 performed by analyzer 32 for each of the carbon dioxide level 196, oxygen level value 212 and nitrous oxide level value 222 calculated as shown in FIG. 9. As shown in FIG. 10, response time protocol 250 receives an input 252 associated with the level values 196, 212, 222 which are associated with the respective gas levels in any given sample. Inputs 252 are verified and adjusted via a physiological mirror 254 as described further below. Protocol 250 calculates a slope sign and magnitude-determined constant K 256 for each input 252 associated with the respective gas. A concentration domain enhancement 258 is generated for each input 252. The slope of the acquired data signal is determined, for example based on the signal change over the last ten samples, and, if the slope is flat or approximates zero, the constant K is chosen to be zero. By first qualifying the state of the rate of change of the signal, analyzer 32 avoids amplifying noise which would occur if a uniform K value were applied regardless of the instantaneous sample change. When the signal slope changes significantly, due to a fast rising or falling edge, constant K is computed to be generally proportional to the slope change of the concentration and proportional to accumulated flow volume up to a maximum allowed value. The interaction of the flow volume in addition to the change in concentration information is used to qualify constant K.

Figure 11:
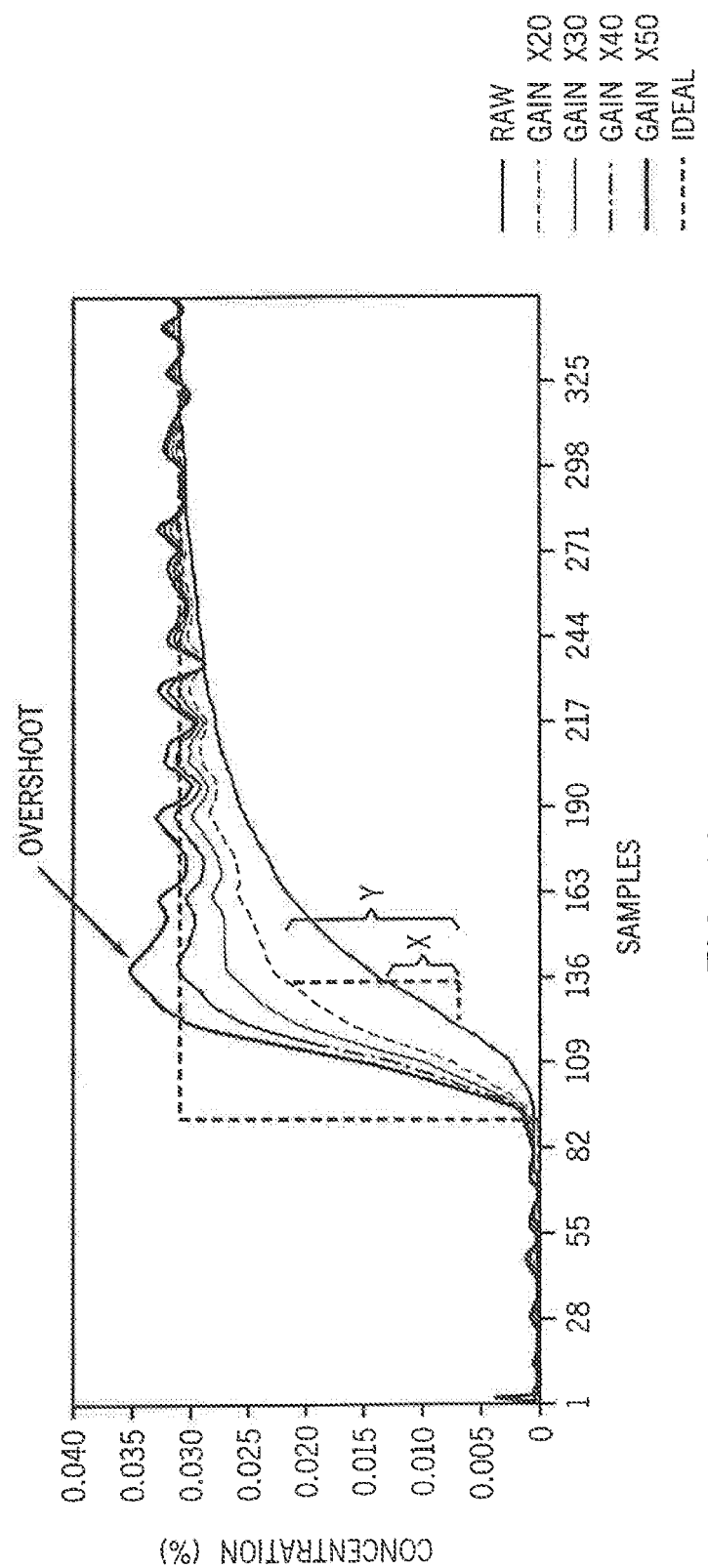
FIG. 11 is a graphic representation of a concentration domain response time enhancement achieved with prior art respiration monitoring systems.

FIG. 11 shows a problem associated with prior art concentration domain response time enhancement procedures that are overcome by the present invention. Usually, a speed-up circuit, or its equivalent in software, is employed in the concentration domain. That is, if the rise at the analyzer is x, then the actual rise at the aspiration location must have been at least y wherein y is a value greater than x. FIG. 11 shows that if gain concentration enhancement of gain times 20 is used, a change in concentration X would result in a reported concentration Y over the same time interval. This approach has severe limitations in that it attempts to compensate a function of concentration versus time by only adjusting the information in one axis. To reproduce a very fast rise, say that which is generated by a square wave input at the aspiration site, overshoot occurs long before a squared output can be obtained. This overshoot is often followed by ringing of the function about the final value before settling occurs thereby detracting from the responsiveness of the system. As shown, simply reducing the gain factor does not reproduce what occurred at the aspiration site but merely reduces the amount of the overshoot and ringing or signal bounce.

Figure 12:
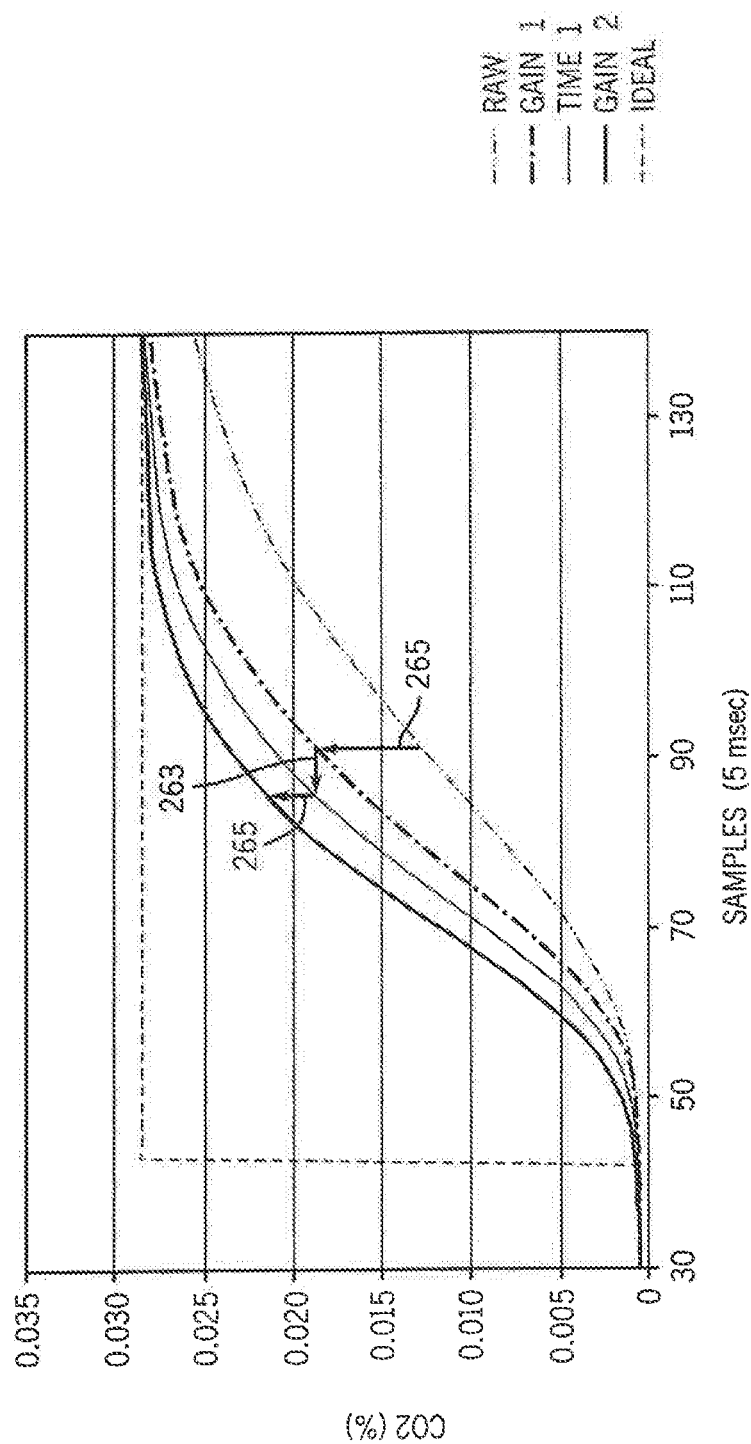
FIG. 12 is a graphic representation of a sample time response time enhancement achieved by the respiration monitoring system shown in FIG. 2.

Referring to FIGS. 10 and 12, unlike the solely concentration domain enhancement results shown in FIG. 11, response time enhancement protocol 250 adjusts for variable gains associated with any of the respective input 252. Having acquired the concentration domain enhancement 258, enhancement protocol 250 performs a time shift of the signal in proportion to the magnitude of slope and a second derivative 262 associated with inputs 252. After the signal is enhanced in the concentration domain, the signal is enhanced in the time domain. Analyzer 32 calculates the first and second derivative of the signal and computes incremental time points from the first and second derivative magnitudes. This manipulation pushes the start of the signal ahead in time, while the upper part of the signal, where the signal begins to plateau, gets retarded in time such that there is no residual time shifting when the slope returns to zero.

As shown in FIG. 12, for samples acquired every five milliseconds, the carbon dioxide trend is adjusted for multiple gains, indicated by arrows 263, 265 across an acquisition cycle. Each correction protocol 188, 190, 192 performed by controller 60 of analyzer 32 is configured to determine a parameter output value by adjusting a value of an input, i.e. the detected value, in both an amplitude domain 265 and a time domain 263. It is appreciated that the amplitude domain 265 can be any of a concentration, a temperature, a pressure, or a flow value associated with the acquired data. It is further understood that when the amplitude domain 265 is a concentration, the associated value is the detected concentration of a gas of interest such as oxygen, carbon dioxide, nitrous oxide, or water vapor. It is further appreciated that each correction protocol 188, 190, 192 be configured to the type of sensor being utilized. That is, the correction protocol will not be the same for a laser-type oxygen sensor as compared to the galvanic-type oxygen sensor.

Figure 13A:
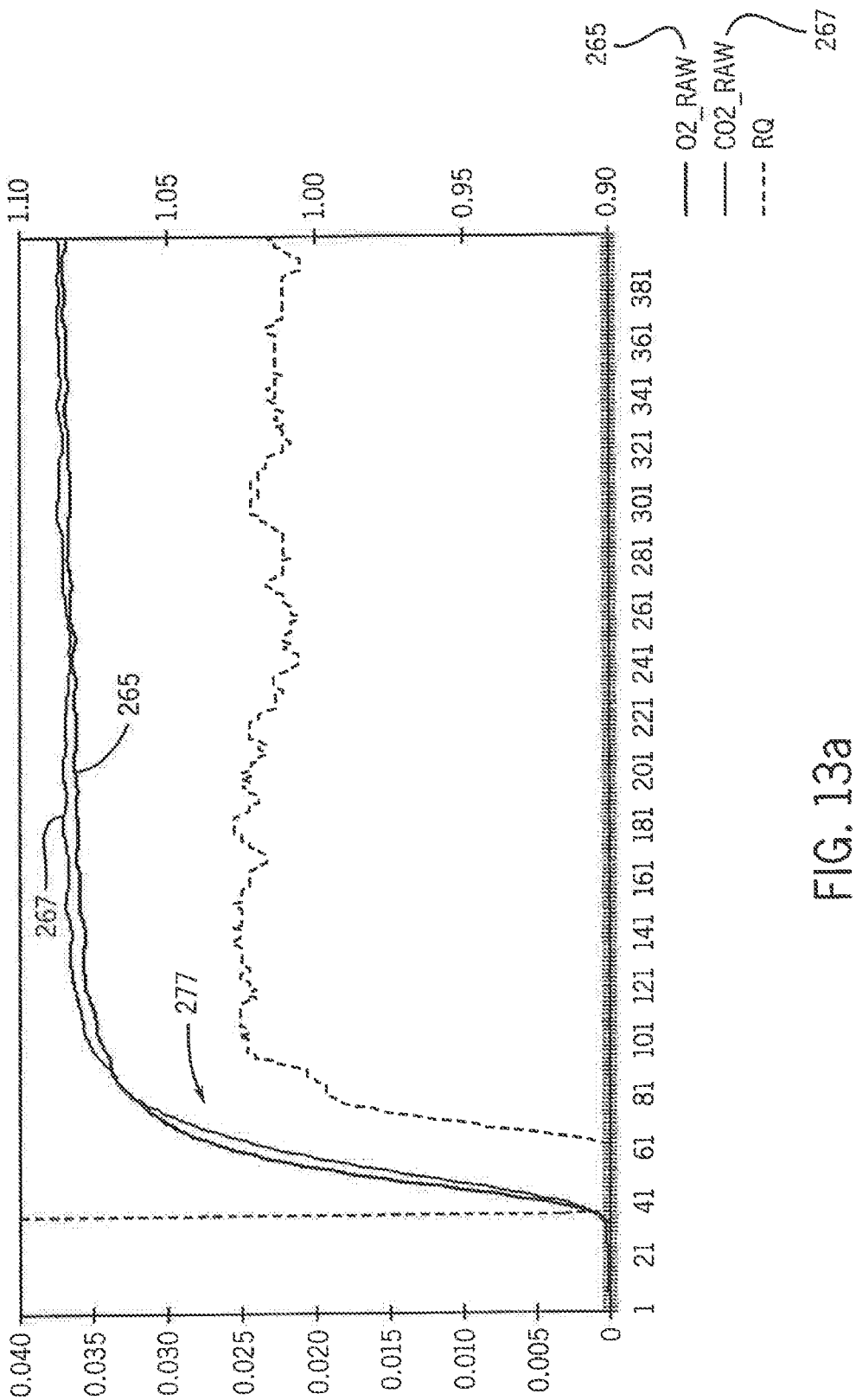
FIGS. 13a and 13b are a graphic representation of a data correction process performed by the analyzer shown in FIG. 3.
Figure 13B:
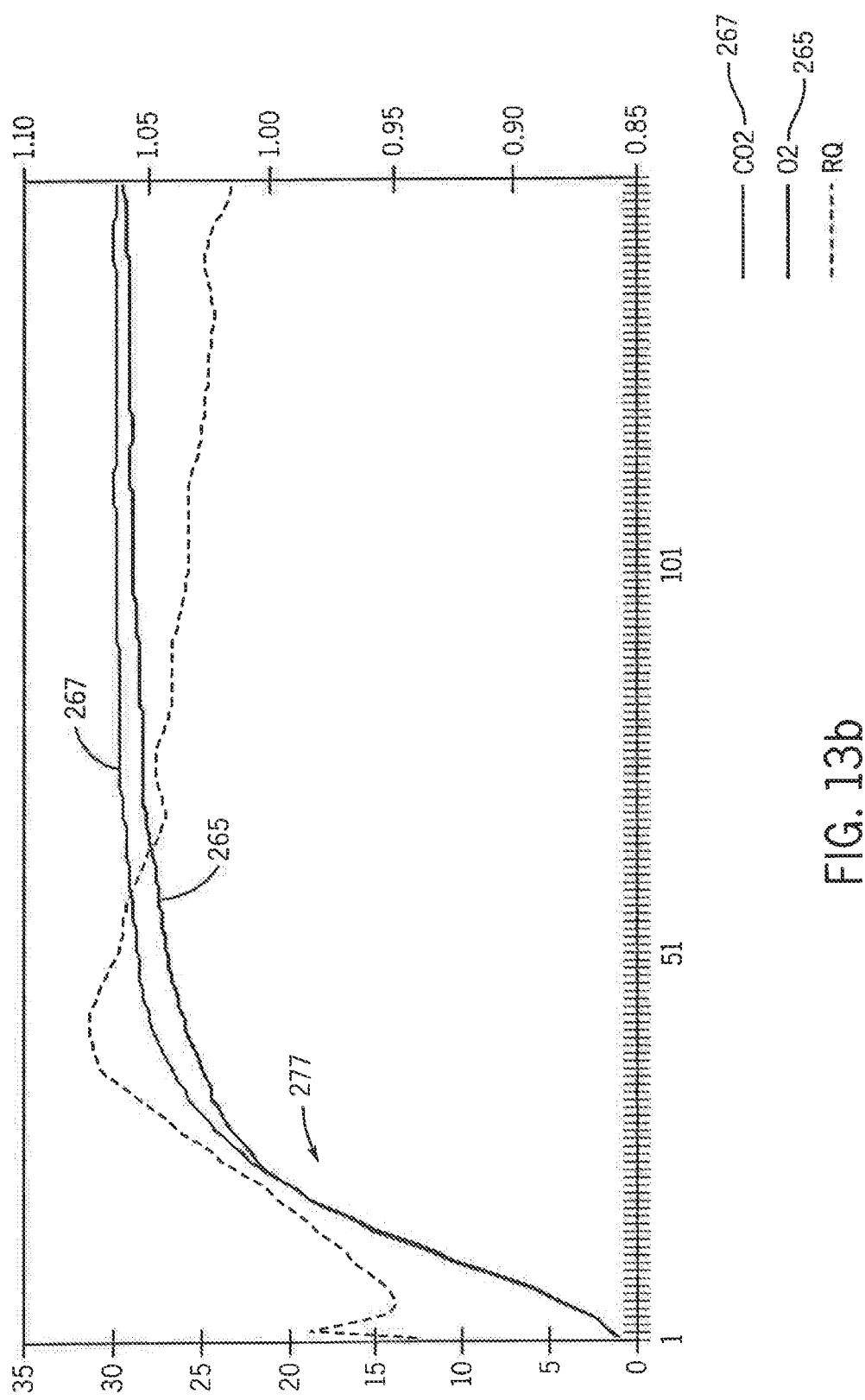

FIGS. 13a and 13b show uncorrected data and an exemplary first corrected output associated with use of a galvanic-type oxygen sensor, respectively. As shown in FIG. 13a, due in part to sensor selection and construction, the responsiveness as well as the gain accuracy of the respective sensors must be corrected. FIG. 13a shows an uncorrected fractional percentage of an oxygen deficit value 265 and an uncorrected fractional percentage carbon dioxide value 267. During a first portion of the data acquisition cycle 277, oxygen sensor 62 is more responsive than the carbon dioxide sensor 64 resulting in oxygen value 265 remaining to the left of the carbon dioxide value 267. After a given period, gain deviation of the oxygen sensor 62 results in the oxygen deficit data value falling below the carbon dioxide value 267. This operational variation of the sensors results in a deviation in the respiratory quotient value. These offsets, generally associated with the operation gain of the sensors, can be accounted for in a relatively simple manner over extended data acquisition cycles, however, these operational variations should be addressed to improve the accuracy of the real-time breath-by-breath monitoring.

FIG. 13b shows an output associated with a first correction of a response time characteristic. As shown in FIG. 13b, adjusting oxygen deficit values 265 during portion 277 of the data acquisition cycle achieves the alignment of the fractional percentage of carbon dioxide value 267 and the deficit fractional percentage of the oxygen value 265 such that the two values generally correlate as determined by the RQ value. During operation, analyzer 32 determines a maximum slope of a leading edge of the acquired oxygen and carbon dioxide values. A difference in the abscissa value associated with a line corresponding to the maximum slope provides an oxygen to carbon dioxide offset value. This offset value is applied to generally align the carbon dioxide and deficit oxygen values over portion 277 of the data acquisition cycle. To align the portion of the acquisition cycle beyond portion 277, analyzer 32 generates a gain prediction associated with operation of each of oxygen sensor 62 and carbon dioxide sensor 64. The oxygen sensor gain value is then determined to account for the deviation between the operation of the carbon dioxide sensor and the oxygen sensor over an extended duration such that the deficit oxygen value correlates to the carbon dioxide value over nearly the entirety of the data collection cycle. That is, the first correction corrects for a response time difference between the pair of sensors and the second correction is different than the first correction and corrects for another response time characteristic, i.e. gain differentiation between the respective sensors.

Referring back to FIG. 10, protocol 250 performs a second physiological mirror 264 on the time adjusted concentration values. Procedure 250 performs a second concentration domain enhancement 266 and a second time domain enhancement 268 time shift in proportion to the magnitude and slope of the second derivative. After the second time domain enhancement 268, protocol 250 again updates the data with a physical mirror check 269 and adjusts the data with a concentration domain enhancement 271 wherein constant K is divided by an exponential increase of half of the constant K utilized at enhancement 258. Process 250 further adjusts the time domain enhancement shift 273 in proportion to the magnitude of the slope and the second derivative prior to completion 275 of the time enhancement protocol 250. Upon completion 275 of protocol 250, analyzer 32 generates a partial pressure compensated gas concentration for each of the inputs 252 associated with the gasses communicated to analyzer 32.

Having corrected the respective gas values for partial pressure and temporal delays in the operation of the sensors 62, 64, 66, analyzer 32 verifies the calculated data through application of a physiological mirror comparison. That is, dynamic alignment is needed to account for differences between internal, pneumatic connections, resistances and dead-space volumes associated with the sample gas acquisition. This compensation becomes more important if there are more than one gas species to be analyzed. It is commonly understood that for every oxygen molecule consumed in a living organism, there is some concomitant generation of carbon dioxide. The exact relationship of these quantities is based upon the stoichiometric relationship of the associated gas. Because the chemical makeup of proteins, carbohydrates, fats, etc. is different the exact relationship of oxygen to carbon dioxide is different. However, there are some aerobic physiologic ranges which cannot be exceeded and therefore generate a physiologic mirror between the associated gases. It is generally accepted that the physiologic mirror of the association carbon dioxide to oxygen during human respiration is approximately between 0.66 and 1.3 for humans at rest.

Analyzer 32 utilizes this physiological mirror to align the signals of different gas sensors as well as for filtering the signals associated with the respective sensors by identifying anomalies in the physiological mirror. Analyzer 32 is preferably configured to acquire and analyze a gas sample every five milliseconds. Analyzer 32 collects and corrects flow and gas concentration data as well as other information such as patient pressure and temperature and computes the carbon dioxide produced and the oxygen consumed for each sample acquired. The division of the carbon dioxide value by the oxygen value provides a respiratory quotient (RQ) for each sample acquired. By calculating the respiratory quotient every sample cycle, any misalignment of the respective outputs of the gas sensors becomes readily apparent and can be adjusted for. This process provides an indication as to the operating condition of the analyzer 32.

Figure 14:
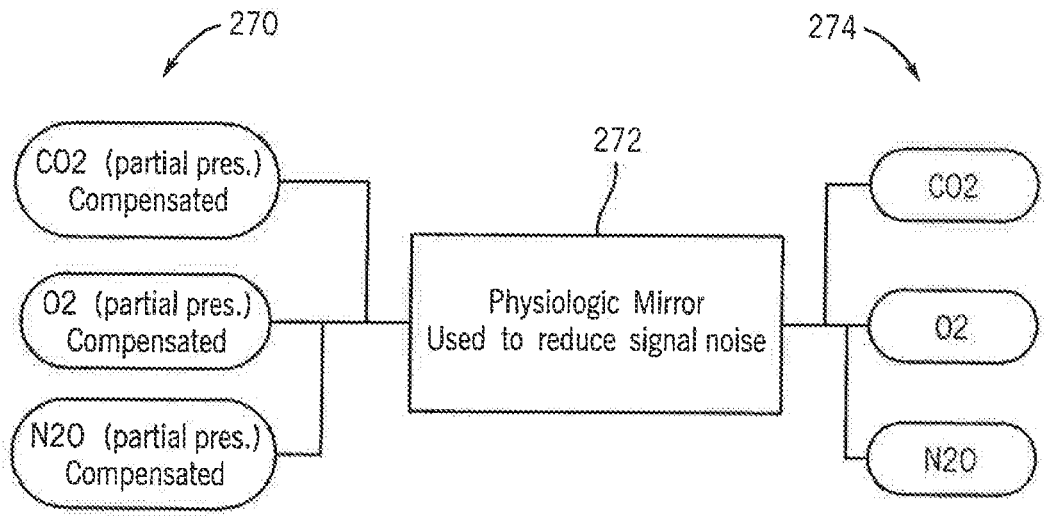
FIG. 14 is a schematic representation of a gas concentration physiological mirror correction procedure performed by the monitoring system shown in FIG. 2.
Figure 15:
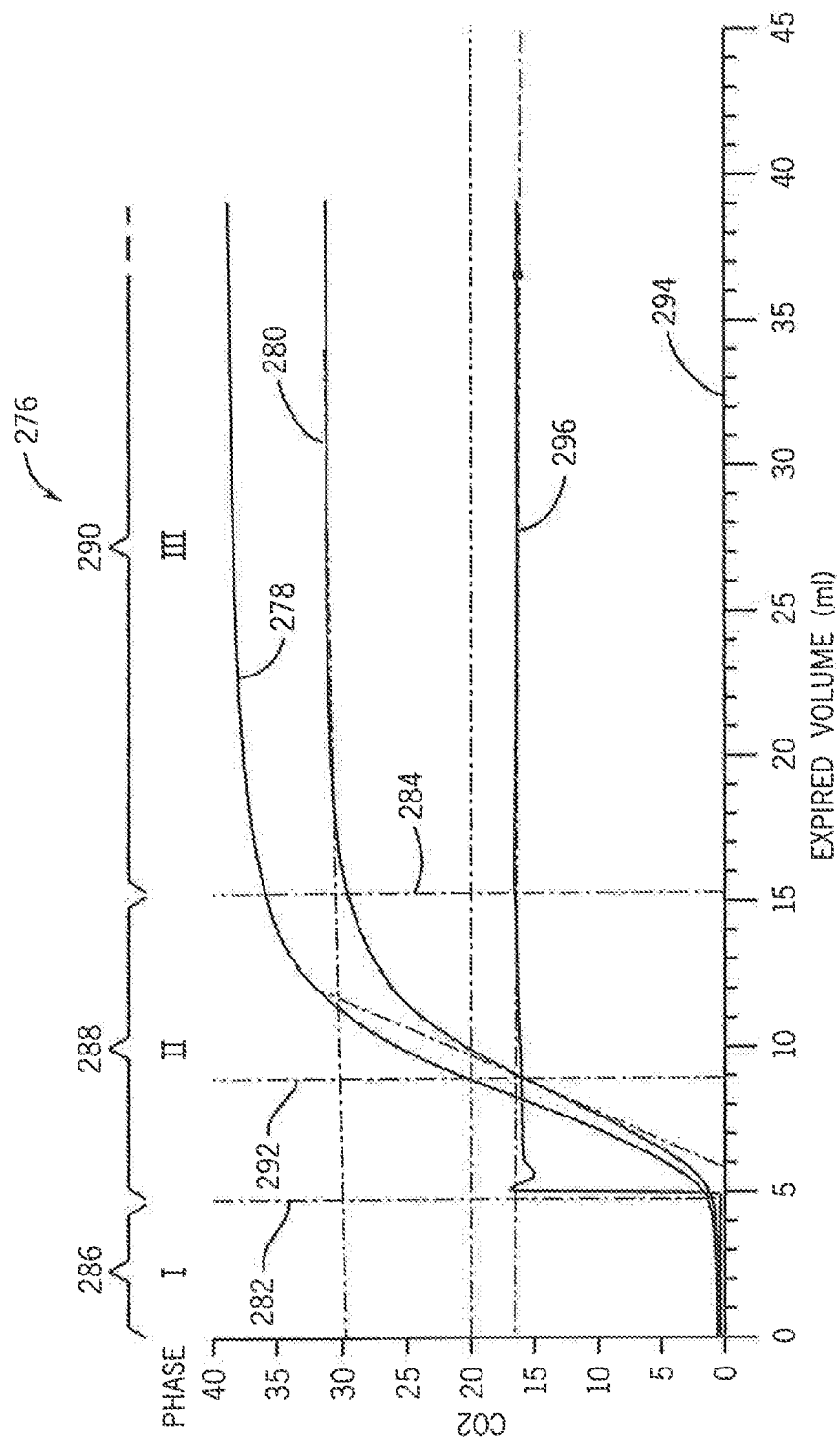
FIG. 15 is a graphic representation of one embodiment of a dead-space correction procedure achieved by the respiration monitoring system shown in FIG. 2.

As shown in FIG. 14, partial pressure compensated values 270 of the respective sample constituents, a process using a physiological mirror 272 as described above to provide a further corrected output 274 associated with each of the respective constituent sample gases. Referring to FIG. 15, analyzer 32 also includes a dead-space compensation protocol. A plot 276 showing an Aitkin dead-space shows one exemplary output associated with a dead-space calculation. Other procedures, such as the Bohr method and/or consideration of a patient's arterial carbon dioxide concentration obtained from blood gas sampling method, are equally applicable to the present invention. Instead of viewing a sample against time, plot 276 shows a gas concentration as a function of expired volume.

The particular breath shown in FIG. 15 shows an oxygen consumption trend 278 which represents inspired volume minus concentration as volume increases. Plot 276 includes an oxygen trend 278 and a carbon dioxide trend 280 associated with a sample breath. Vertical lines 282, 284 represent transition positions of the breath phase. The left of vertical line 284 is a first phase 286 that represents an absolute dead-space. A second phase 288 between vertical lines 282 and 284 generally occurs over a relatively short period of time with the gas concentration rapidly changing as a function of time. A third phase 290, to the right of vertical line 284, represents that area of a breath cycle wherein the concentration plateaus or only slowly increases while volume continues to accumulate. Vertical line 292, generally between vertical lines 282 and 284 delineating phase II 288 from phase I 286 and phase III 290, represents the Aitkin dead-space. The volume, that point where vertical line 292 intersects abscissa 294, represents the breath dead-space and is a combination of absolute and physiologic dead-space.

The respiratory quotient (RQ) as explained above is represented on plot 276 at line 296. RQ 296 represents the ratio of carbon dioxide volume to oxygen volume for the breath represented in plot 276. Analyzer 32 continually monitors RQ 296 with respect to the detected values of oxygen 278 and carbon dioxide 280 such that an anomaly in either of oxygen trend 278 or carbon dioxide trend 280 would be represented in a time-aligned anomaly in RQ 296. Upon the detection of an anomaly in RQ 296, analyzer 32 verifies the accuracy of oxygen value 278 and carbon dioxide value 280 to auto-correct an oxygen value or a carbon dioxide value that does not correspond to the RQ value as determined from the time aligned physiological mirror of the corresponding breath oxygen value and carbon dioxide values.

Figure 1:
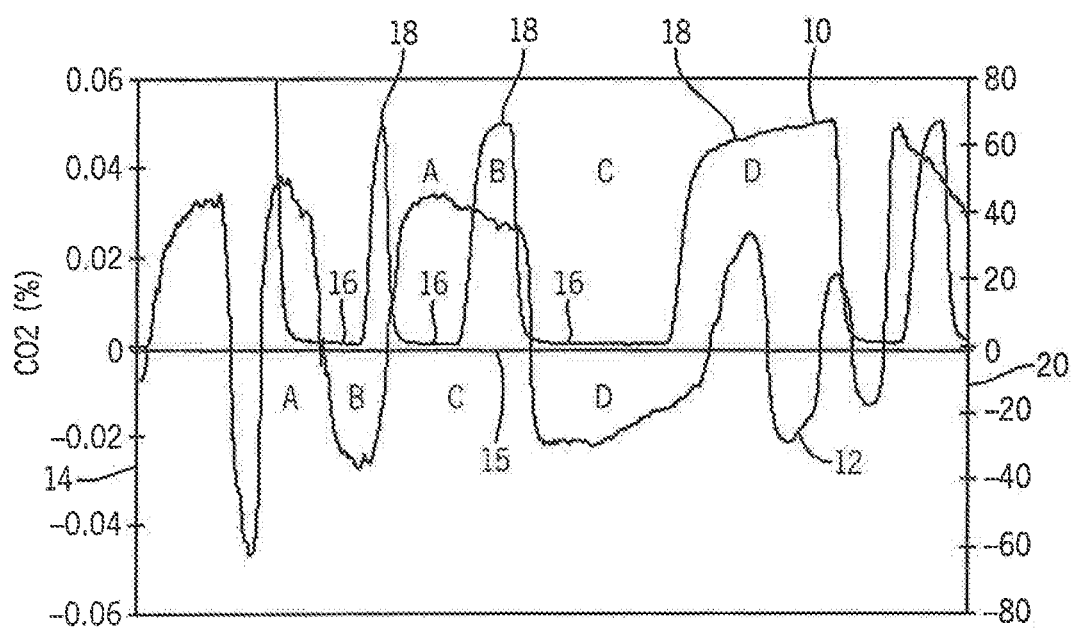
FIG. 1 is a schematic representation of data representation of prior art devices.
Figure 16:
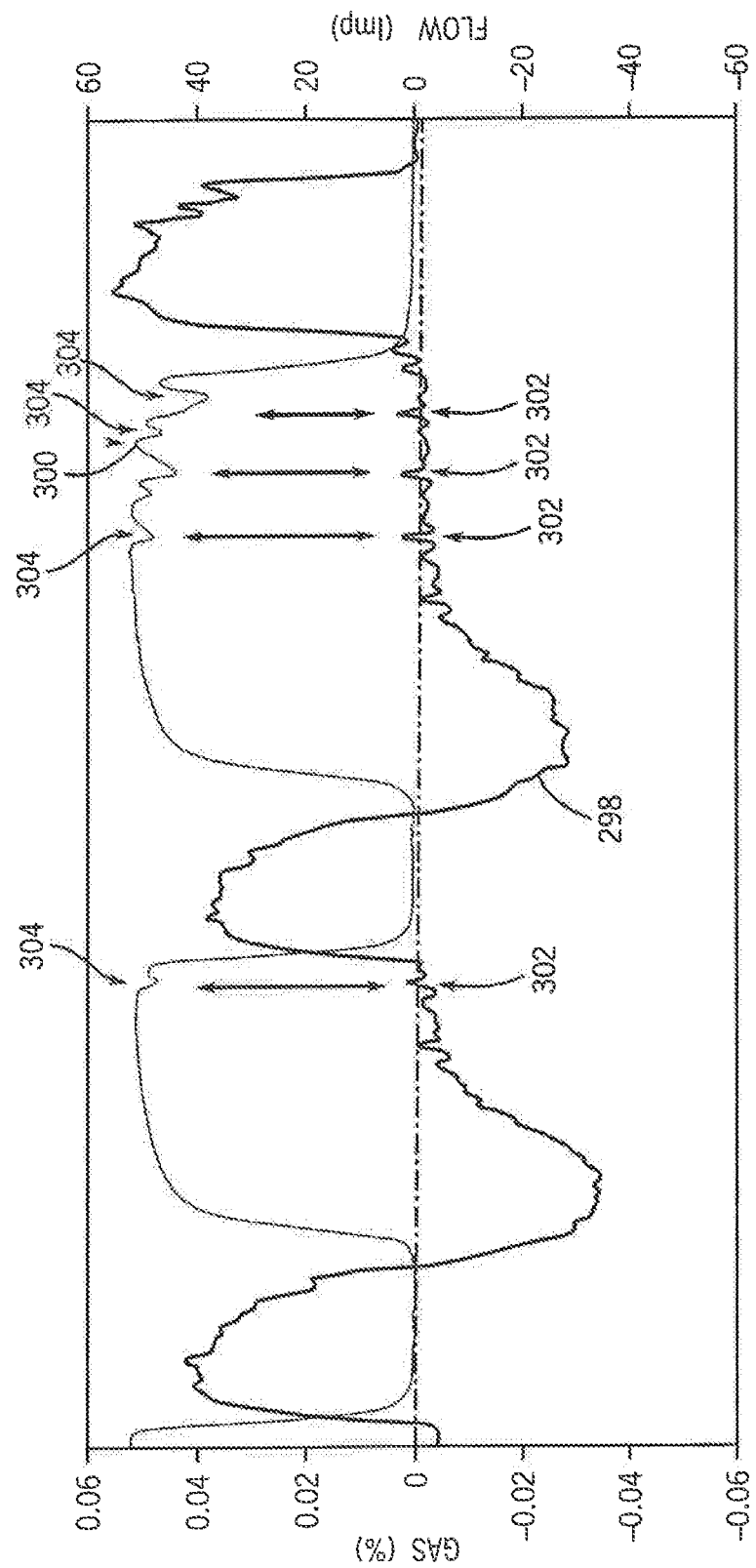
FIG. 16 is a graphical representation of a flow reversal synchrony that shows the time aligned flow and gas concentration values achieved by the respiration gas monitoring system shown in FIG. 2.

In addition to the physiological mirror, dead-space, and response time enhancements discussed above, analyzer 32 includes a flow reversal protocol (FRP) as graphically represented in FIG. 16. Comparing FIGS. 1 and 16, it is shown that analyzer 32 performs a flow reversal synchronization of the trends associated with flow 298 and a gas concentration value 300. As shown in FIG. 16, pulsatile effects 302 monitored by the flow generally correspond to pulsatile effects 304 monitored in the gas value 300. Accordingly, temporally-aligning the pulsatile effects 302 in the flow 298 with the pulsatile effects 304 in the gas value 300 provides for temporal alignment of the respective trends associated with both flow and gas concentration value. As will be described further below with respect to FIG. 21, such alignment provides a well-organized and readily understandable flow and concentration output as compared to that which is generally shown in FIG. 1.

As disclosed further below with respect to FIGS. 22-26, situations can exist wherein pulsatile effects 302 are so minimally represented in the acquired and calculated flow and composition data that an alternate approach is desired to ensure the accuracy of the time domain flow and composition data. As disclosed below with respect to FIGS. 22-26, when desired, analyzer 32 introduces an extraneous signal to respective breath respiration flows associated with the respective sensor such that the acquired respiration flow information includes information that is indicative of the extraneous alignment signal. As disclosed further below, this non-patient originated alignment signal is introduced to the respiration flow via the sensor at desired intervals such that the information associated with the alignment signal can be easily ascertained from the respiration flow and composition data acquired by analyzer 32 to effectuate a time-wise or time domain alignment between the respiration flow and respiration composition information.

Figure 17:
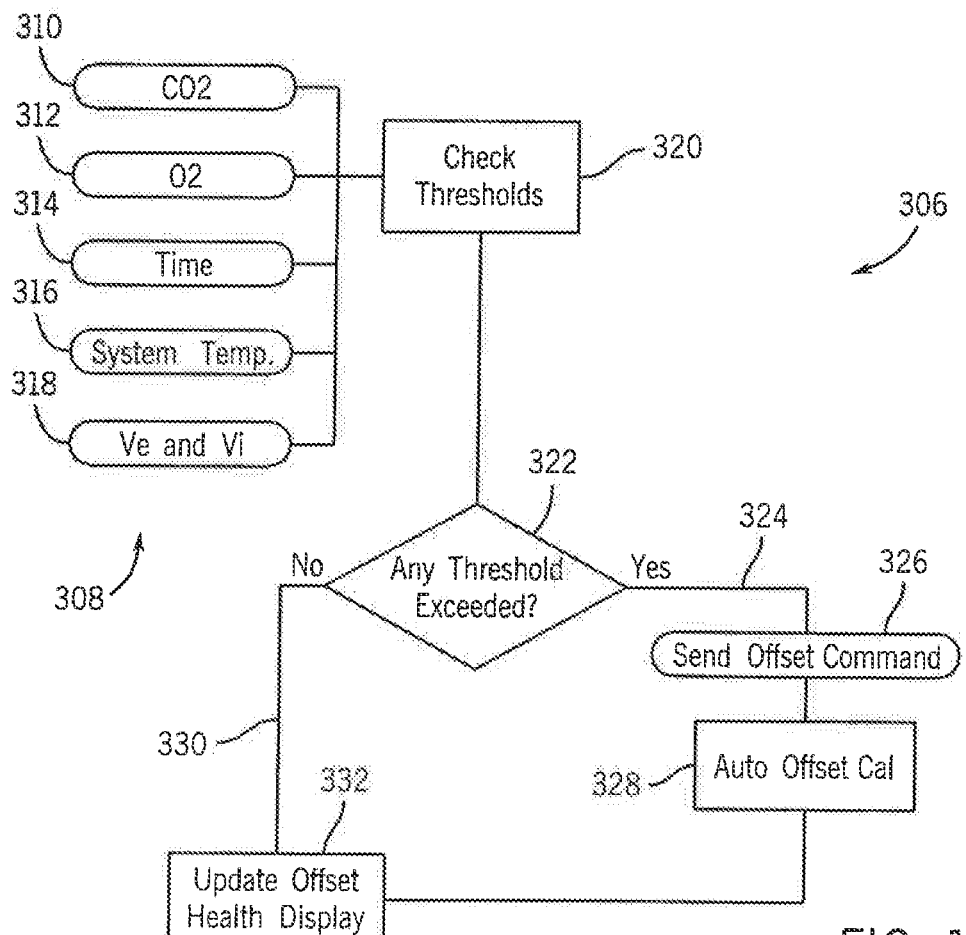
FIG. 17 is a schematic representation of a threshold calibration and check procedure performed by the respiration gas monitoring system shown in FIG. 2.

Analyzer 32 also includes a number of other calibration and operation procedures as shown in FIGS. 17-20. Referring to FIG. 17, analyzer 32 includes a threshold confirmation protocol 306 wherein, during operation, analyzer 32 receives a plurality of inputs 308 associated with a carbon dioxide value 310, an oxygen value 312, a time value 314, a system temperature value 316 and a signal input value 318. Understandably, other inputs could also be provided to analyzer 32. Threshold confirmation protocol 306 automatically checks to confirm that thresholds associated with any of the inputs 308 do not exceed or otherwise not satisfy desired threshold values. It is further understood that each of the thresholds associated with threshold confirmation protocol 306 can be configured by a user to a desired value. Threshold confirmation protocol 306 determines if any of the checked thresholds 320 are exceeded 322. If any of the desired thresholds are exceeded 324, protocol 306 delivers an offset command to a user 326 and/or performs an automatic offset calibration 328 as described further below. In the event that no threshold is exceeded during operation of the analyzer 32, the analyzer updates the offset health display 332 associated with the checked thresholds 330.

Figure 18:
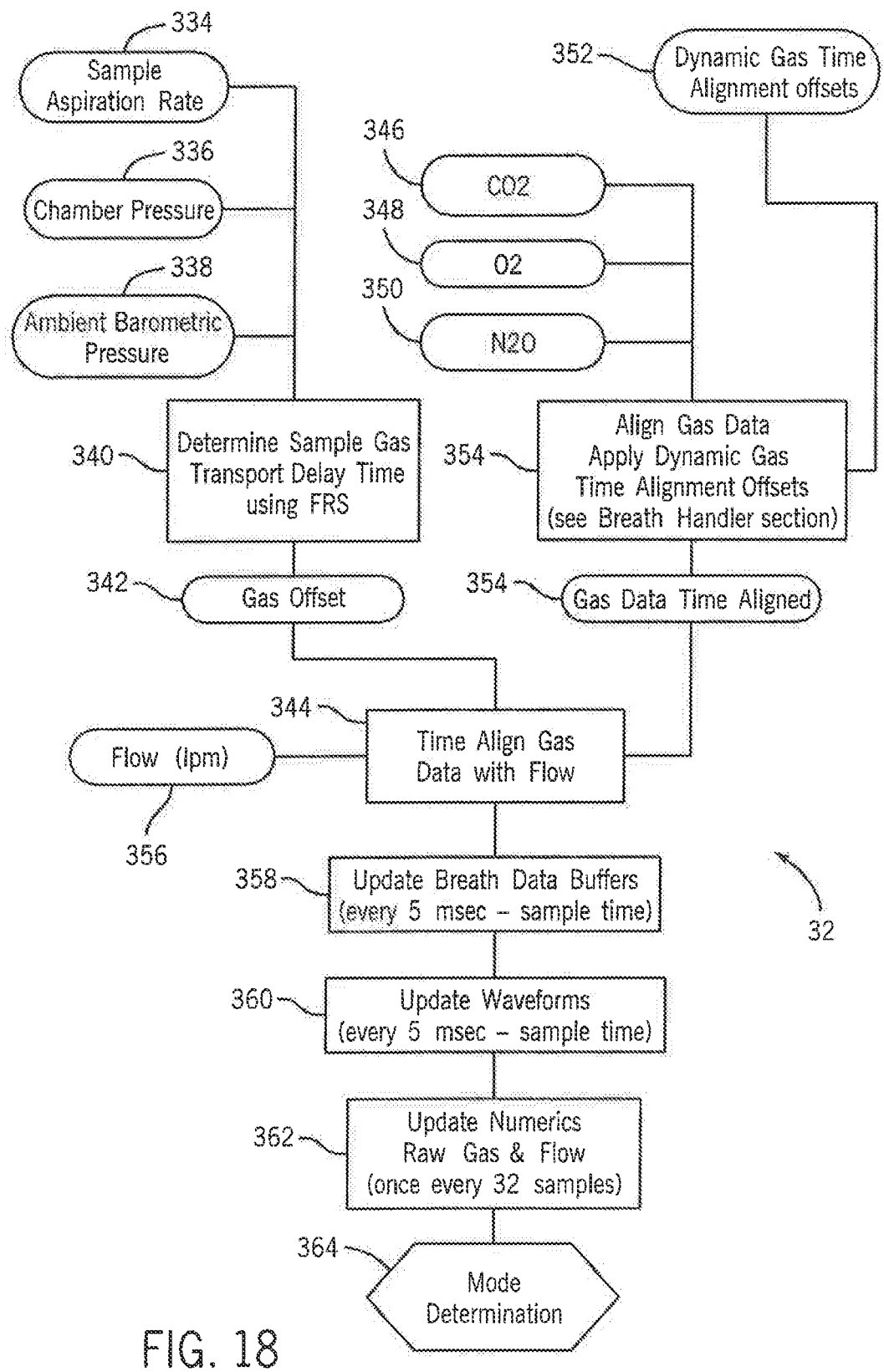
FIG. 18 is a schematic representation of an ambient condition flow and gas concentration alignment procedure performed by the respiration gas monitoring system shown in FIG. 2.

Referring to FIG. 18, analyzer 32 calculates a sample aspiration rate 334, detects an analyzer pressure 336, an atmospheric pressure 338, determines a sample gas transport delay time, and implements the flow reversal synchronology 340 as described above with respect to FIG. 16. Analyzer 32 then generates a gas value offset 342 which is utilized for time alignment of gas data with flow data 344. Analyzer 32 detects a carbon dioxide value 346, an oxygen value 348 and a nitrous oxide value 350 in conjunction with the dynamic gas time alignment offsets 352 as discussed above with respect to FIGS. 12-15, finds the gas data 354 and communicates the time aligned gas data 354 and the flow data 356 to time align the gas and flow data 344. Preferably, analyzer 32 updates the breath data buffers sample every five milliseconds 358 and updates the waveforms 360 associated with the time aligned gas and flow data 344 for every sample as well. It is appreciated that other breath data buffer update and time alignment schedules may be utilized that are more or less frequent than the preferable five millisecond and every breath sample intervals disclosed above.

Figure 19A:
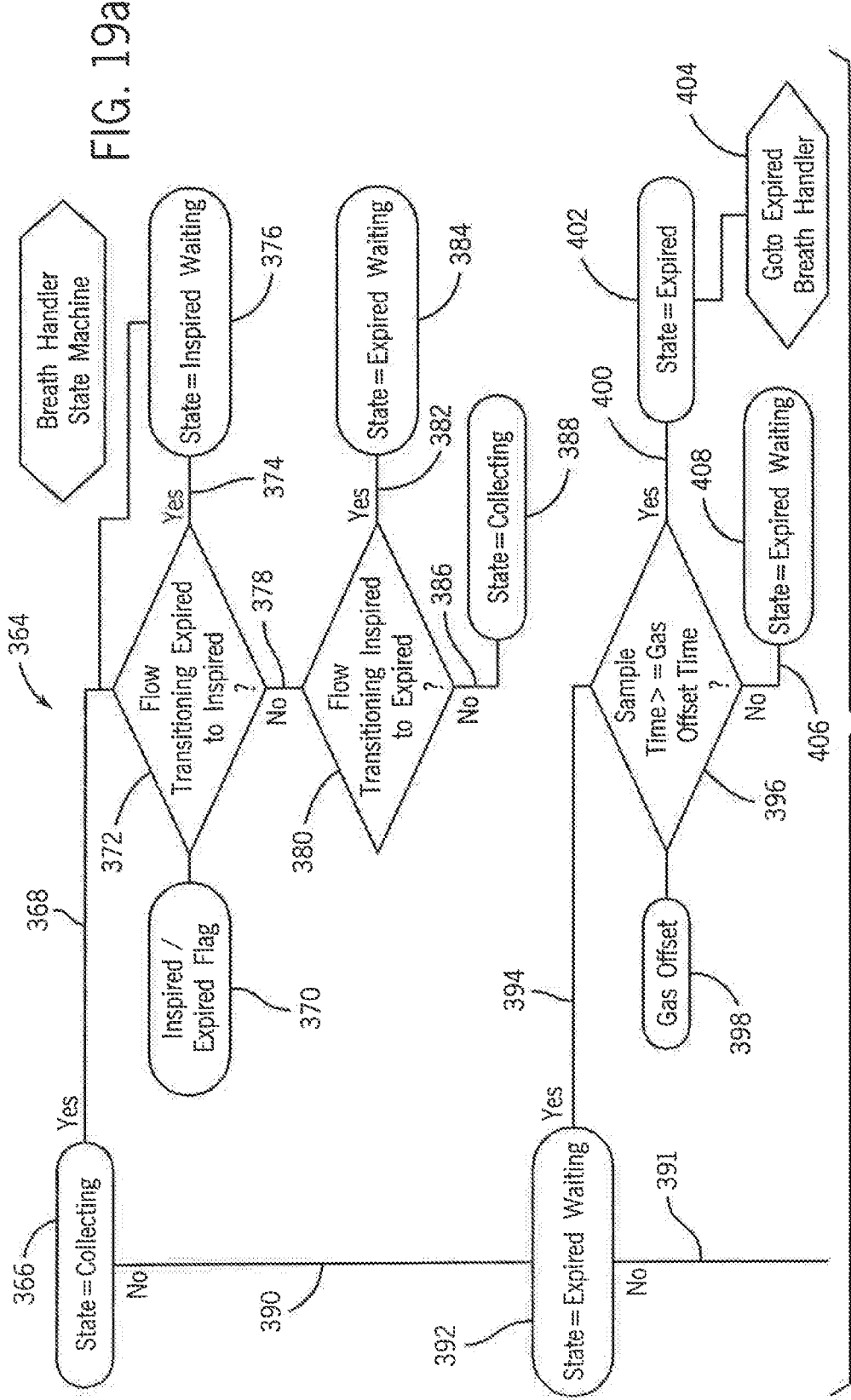
FIGS. 19a and 19b are a schematic representation of a flow cycle determination and correction procedure performed by the respiration gas monitoring system shown in FIG. 2.
Figure 19B:
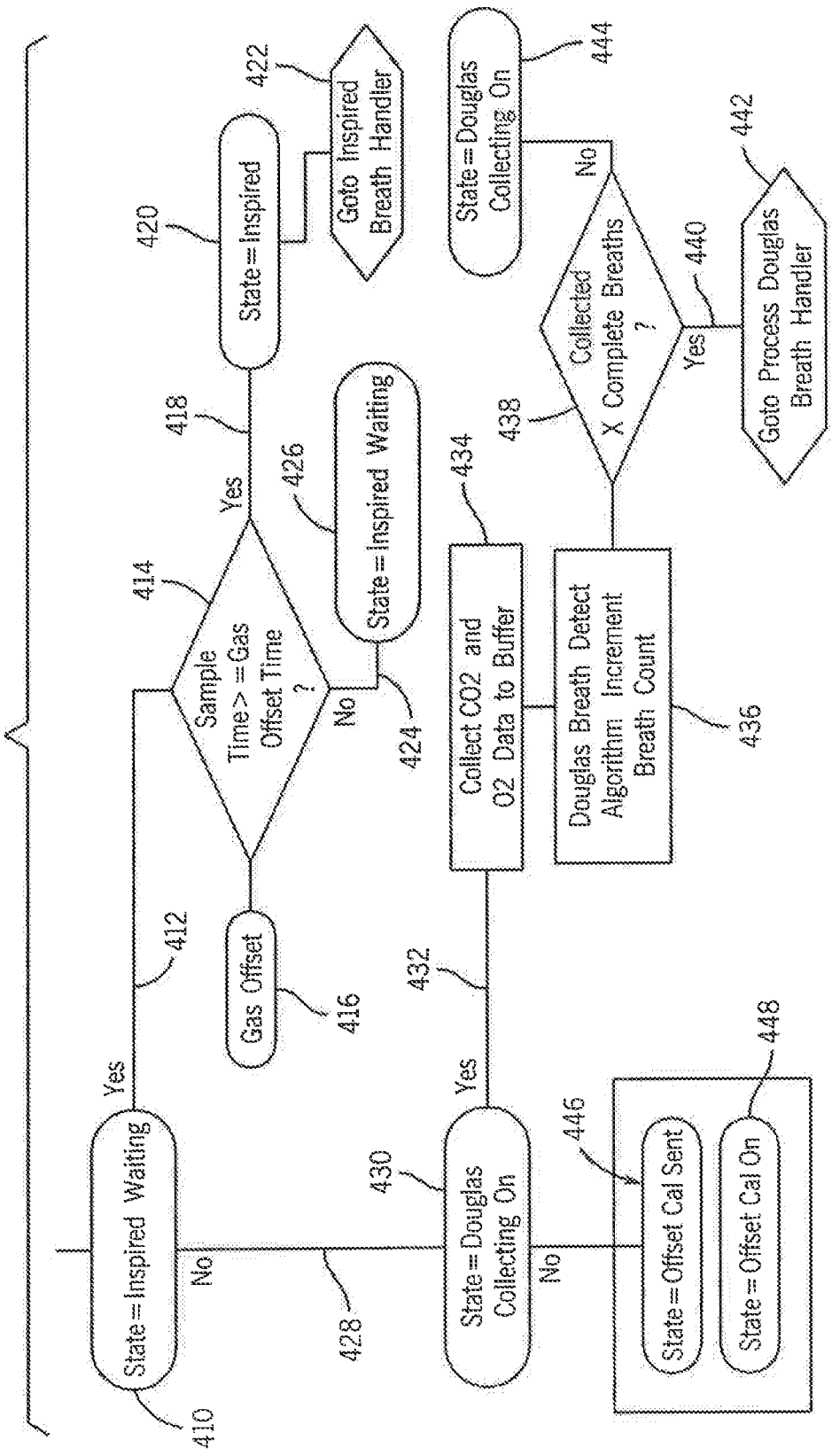

Approximately every 32 samples, analyzer 32 optionally updates the numerics associated with the raw gas and flow data 362 as a service performance monitoring function to allow background monitoring of the performance of analyzer 32. The information associated the system performance monitoring function may occur at any given interval and may be hidden from a user and accessible only in an analyzer service or monitoring window separate from the respiration data window associated with display 36. Analyzer 32 next performs a mode determination 364. As shown in FIGS. 19a and 19b, mode determination 364 includes a determination 366 as to whether the analyzer 32 is collecting data. During collection of data 368, mode determination 364 monitors an inspired/expired flag 370 to determine a flow transition from an expired to an inspired flow direction 372. If the flow is transitioning from an expired to an inspired flow direction 374, mode determination 364 provides a delay 376 to wait for an inspired value. The flow is not transitioning from an expired to an inspired flow 378, mode determination 364 determines whether flow is transitioning from inspired to an expired flow 380. If the flow is transitioning from an inspired to an expired flow 382, mode determination 364 enters an expired waiting state 384. And if the flow is not transitioning from inspired to expired flow 386, mode determination 364 confirms a collecting state 388.

Figure 20A:
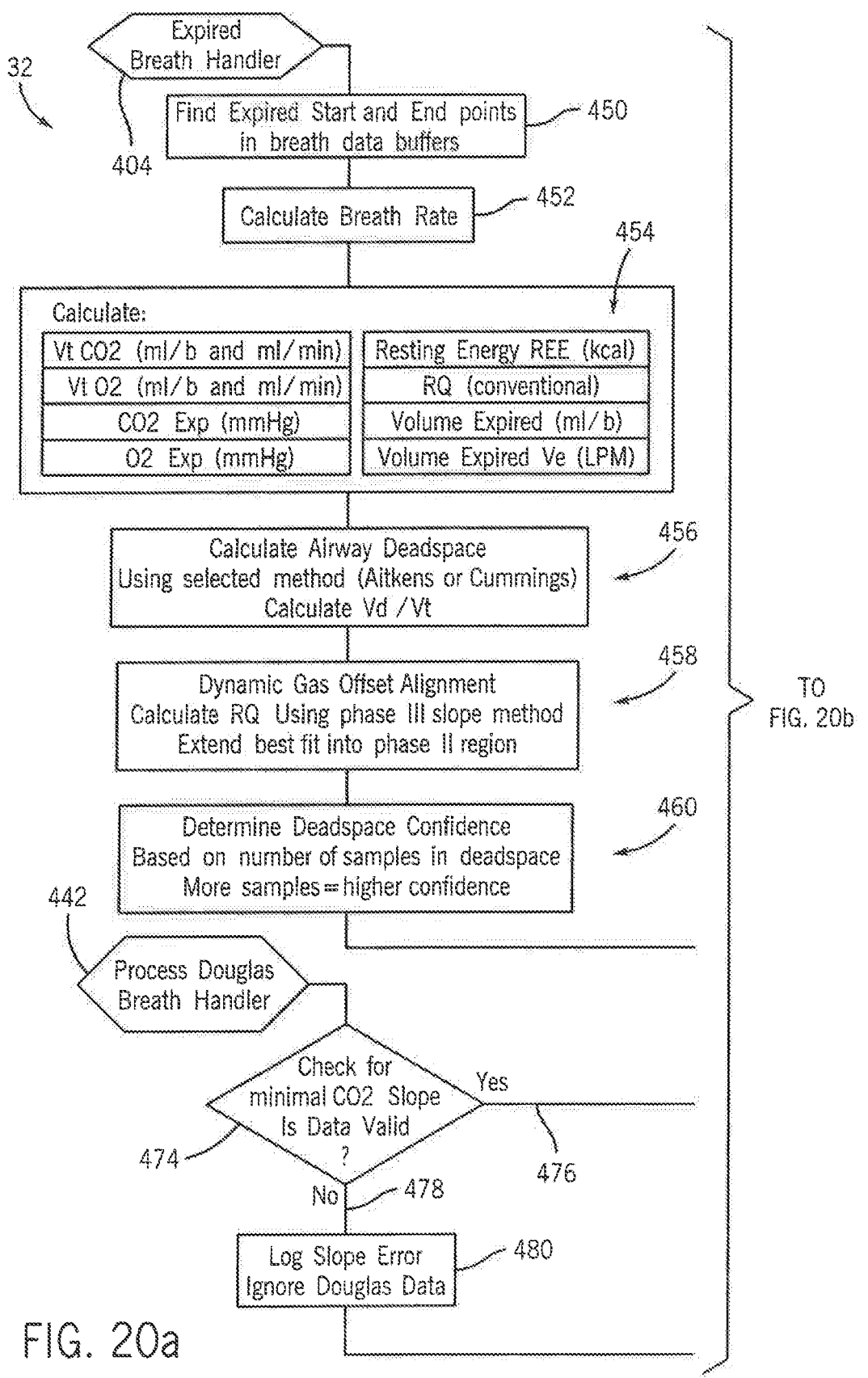
FIGS. 20a and 20b are a schematic representation of a time aligned respiration information generation procedure that accounts for the flow cycle determination and correction procedure shown in FIGS. 19a and 19b.
Figure 20B:
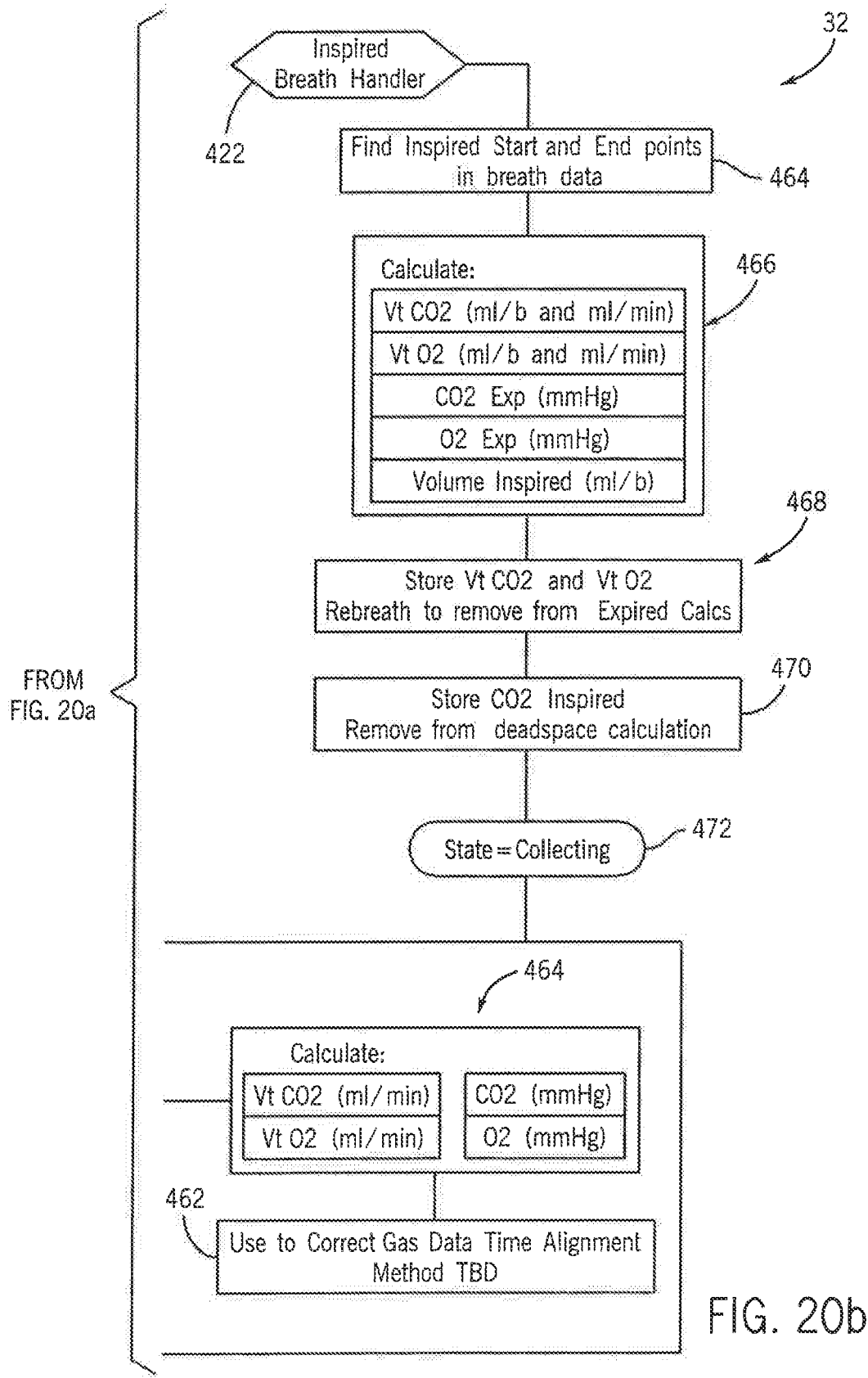

When mode determination 364 is not in a collecting state 390, mode determination 364 determines whether it is an expired waiting state 392 and, if so, 394 monitors a sample time as compared to a gas offset time 396 associated with an inputted gas offset 398. If the sample time is greater than a gas offset time 400, mode determination 364 associates the state as expired 402 and directs operation of analyzer 32 to expired breath handling 404 as shown in FIGS. 20a and 20b. When the sample time is not greater than the gas offset time 406, mode determination 364 is directed to an expired waiting 408 state. If mode determination 364 is not in a collecting state 390 and is not in an expired waiting state 392, mode determination 364 determines an inspired waiting state 410. And if the mode determination 364 is in an inspired waiting state 410, 412, mode determination 364 determines whether a sample time is greater than or equal to a gas offset time 414 as determined by gas offset 416. The sample time is greater than the gas offset time 418, mode determination 364 confirms an inspired state 420 and directs operation of analyzer 32 to inspired breath handling 422 mode as shown in FIG. 20b. If the sample time is not greater than or equal to the gas offset time 424, mode determination 364 maintains an inspired waiting state 426.

If analyzer 32 is not in a collecting state 390, not in an expired waiting state 391, and not in an inspired waiting state 428, mode determination 364 automatically checks a Douglas collecting state 430. When analyzer 32 detects the connection to a Douglas bag collecting system 432, analyzer 32 collects gas from the Douglas bag 434 and performs a Douglas breath detect algorithm and increment breath count 436 to mimic a breath cycle when analyzer 32 is connected to a Douglas bag. When Douglas collecting state 430 is activated, analyzer 32 determines whether a desired number of breaths have been collected 438 and, if so, 440 directs mode determination 364 to Douglas bag breath handling 442 as shown in FIG. 20*a*. Analyzer 32 maintains Douglas collecting state 430, 444 until a desired number of breaths have been collected. Upon confirmation of a no collection mode determination 364, analyzer 32 further includes a number of offset calibration options 446, 448 utilized to not process breath data during offset calibration of analyzer 32. Such a configuration allows analyzer 32 to be configured for operation with offset calibrations as may be required by any particular patient.

FIGS. 20*a* and 20*b* show the initialization calibration procedure associated with expired breath handling 404, inspired breath handling 422 and Douglas bag breath handling 442. When analyzer 32 begins in expired breath handling 404, analyzer 32 determines expiration start and end points associated with the breath data buffers 450. Analyzer 32 determines a breath rate 452 and calculates a plurality of parameters associated with an acquired sample value 454. Analyzer 32 then calculates the sample values 454, patient or respiration path dead-space 456, and dynamically aligns the gas offset 458 using the calculated RQ and the calculated dead-space 456. During expired breath handling 404, analyzer 32 determines a dead-space confidence 460 determined by a number of dead-space values for each associated sample. Having adjusted for dead-space variations, expired breath handling 404 corrects gas data with time alignment 462 utilizing any of the methods discussed hereabove and then calculates 464 volumes and pressures associated with the constituents of the sample acquired.

Comparatively, inspired breath handling 422 determines an inspired start and end points in breath data of the sample acquired, calculates 464 the volume and pressure of the constituents of the acquired sample 466, stores the calculated values and performs a rebreathe operation to remove previously acquired calculations 468. Inspired breath handling 422 stores an inspired carbon dioxide value 470 and adjusts the inspired carbon dioxide value from the dead-space calculation as previously described with respect to FIG. 15. Inspired breath handling 422 confirms a collecting state 472 and proceeds to correct gas data time alignment 462 and calculations 464.

During Douglas bag breath handling 442, analyzer 32 performs a minimal carbon dioxide slope check 474 and if the acquired carbon dioxide value is valid 476, Douglas bag breath handling 442 proceeds to calculations 464. If the carbon dioxide slope data check 474 is invalid or below a desired threshold 478, Douglas bag breath handling 442 maintains slope error data and disregards the determined Douglas bag data in proceeding to the correct gas data time alignment 462 and calculation 464. Accordingly, regardless of where in a respiration cycle analyzer 32 begins data acquisition, analyzer 32 auto-corrects for various parameters that can be acquired during any given phase of the respiration cycle.

As previously mentioned, collecting a patient's expired gases allows analyzer 32 to perform time-independent analysis of a gas source. When connected to a Douglas bag and a sensor 34, analyzer 32 periodically switches from measuring the patient to measuring the gases from a collection vessel for a brief time, thereby performing a time independent RQ determination. Any error between the instantaneously calculated or real-time RQ value and the Douglas Bag RQ value can be used to make finer adjustment to the instantaneously calculated RQ value. The collection vessel can simply be connected to the exit port of a ventilator, connected directly to a patient flow thereby circumventing any ventilator mixing, or other adequately purged collection vessels. It is further envisioned that analyzer 32 be configured to automatically acquire the Douglas bag sample thereby eliminating any clinician intervention and rendering very accurate trend Douglas bag RQ data.

Still referring to FIGS. 20*a* and 20*b*, analyzer 32 further includes several breath alignment correction procedures and calibration procedures. A first breath alignment correction is a flow aspiration correction procedure. A sample gas flow being, aspirated from the flow path of sensor 34 is calculated by analyzer 32 and the corresponding breath parameters are adjusted for the sensor aspirated gas values. The sensor aspirated gas causes an error in the patient flow measurement that must be corrected. Since the location of the sensor 34 gas sampling tube 48 (shown in FIG. 6*a*) is between the tubes 44, 46 (also shown in FIG. 6*a*) used for the flow measurement, the error is asymmetric and opposite in direction depending on whether the patient flow is an inhalation or an exhalation and is a function of the magnitude of the patient respiration flow. If the gas were removed further down stream after the flow ports, this correction to the flow measurement would not be necessary, but an additional time domain shift would be required. In either case, if the patient flow is not significantly greater than the aspiration flow, such as in the case of monitoring small infants, entrainment will occur which must also be addressed.

In the case where the gas is being aspirated between the flow measurement ports, the gas being aspirated produces a pressure drop that is unequal across the ports and is direction dependent that appears as patient flow. Also, the flow error, while proportional to the aspiration rate, is not the same as the aspiration rate. For example, if one is aspirating at 200 ml/min (0.2 lpm), simply adding 0.2 lpm back into the patient flow reading does not adequately reflect the required correction. The error, however, is proportional to the aspiration rate as well as the patient flow rate, and changes with patient flow direction. Analyzer 32 empirically determines the magnitude and direction of the necessary corrections needed to correct the flow readings for this sensor aspiration.

As the patient flow becomes small or approaches zero, the aspiration flow becomes more significant and a condition known as entrainment occurs. Here, the amplitude of the gas signals becomes diluted with other gasses. For example, if the patient gasses are being expired at a low flow rate compared with the aspiration rate, a portion of the sample being aspirated may be redirected into the analyzer. The measured patient flow and controlled and measured aspiration flow is used to determine the true concentration of the patient gas as communicated to the gas sensors. This type of flow correction generally only needs to be performed on infant and premature infant flow levels, as the transitions such pediatric breathing occurs too quickly to be determined by a digitizing sample rate of preferably 5 msec per sample acquisition.

Analyzer 32 includes a dead-space confidence qualifier procedure that is generally applicable with very high breath rates and low dead-space quantities, such as with infants, wherein the total time involved in measuring the dead-space is very short. In such a situation, the time from the flow crossing or start of expiration until the phase II 288 dead-space point 284 may be so short that the insufficient data samples are acquired. If very few data samples are captured during this time, the dead-space confidence qualifier provides feedback to the technician as to the level of confidence in the result. The confidence is based on how many samples, approximately 1 sample every 5 milliseconds, are captured within the dead-space time as calculated using the Aitkin method as shown in FIG. 15. Indicator colors such as green for a high or good level of confidence, yellow for caution, and red for warning may be utilized in display 36 as described below with respect to FIG. 21. It is envisioned that greater than 10 samples would produce a high or good level of confidence, 3 to 10 samples would warrant a caution, and less than 3 samples should produce a warning as to the quality of the dead-space qualifier. The color is used for either the display of the dead-space qualifier itself or as the background color highlighting the dead-space numerical display.

Analyzer 32 also includes a flow offset drift compensation procedure. Analyzer 32 monitors patient respiration flow using a differential pressure transducer connected to sensor 34. The pressure transducer is generally sensitive to changes in temperature. A standard pressure/temperature calibration is performed which characterizes the transducer. In addition, a flow offset drift compensation is performed in an attempt to minimize the zero (offset) error due to changes in temperature between offset calibrations. The method used characterizes pressure vs. temperature using a second order polynomial. Using this equation, a prediction is made of what the pressure would be as temperature changes for the "zero" pressure from the zero pressure determined at the last offset calibration. The flow offset drift compensation procedure acquires an offset calibration temperature T0 and acquires a second temperature TX during acquisition of the flow sample. Analyzer 32 calculates pressures P0 and PX using T0 and TX and then calculates an offset pressure, Poffset, as the difference between P0 and PX. Analyzer 32 subtracts Poffset from the sampled pressure prior to calculating patient flow thereby correcting for flow offset drift.

Analyzer 32 is also configured for automatic calibration of operation of the analyzer 32 and sensors 62, 64, 66. Preferably, sensors 62, 64, 66 are chosen to be inherently gain stable. The gain stability is due to the fact that the sensors have a high degree of resolution at the lower end of their measurement range and lesser resolution towards the upper end. This is desirable since most of the time measurements will be made in the lower part of the range of the respective sensors 62, 64, 66. Understandably, with higher resolution, sensor drift becomes more apparent. The present invention communicates atmospheric air through housing 58 of analyzer 32 to correct for offset drift automatically using an inexpensive calibration gas, i.e. room air.

The room air communicated through housing 58 is utilized as an inhalation sample and a mixed gas having a known composition and or respiratory quotient is communicated to analyzer 32 to provide an exhalation sample. The ambient oxygen concentration is calculated by correcting the ambient oxygen value measured by oxygen sensor 62 for ambient water vapor dilution through utilization of the information detected by temperature and humidity sensors 78, 80 shown in FIG. 3. The room air is also passed through a carbon dioxide scrubber to insure a zero carbon dioxide value. The concentration of the known gas is entered by an operator. Preferably, the concentration of the constituents of the mixed gas is selected such that a result respiratory quotient is within a normal physiological range. One of valves 72, 74, 76, 89, or an additional valve, and pump 70, or another supplemental pump, cooperate to switch the source of gas communicated to sensors 62, 64, 66 between the mixed gas and the room air.

Preferably the mixed gas is provided at a flow rate that is greater than a sample aspiration rate with the excess gas being vented. A pneumatic venturi device is connected between analyzer 32 and the inlet of the mixed gas and creates a pressure differential perceived by flow sensor 67. According, analyzer 32 mimics a breath cycle with real-time operation feedback and detectable gas transitions. It is further understood that, by aligning the artificially developed flow indication with a measured patient flow level, the operability of flow sensor 67 can be confirmed as well as providing a confirmation that the flow of mixed gas is accurately detected by flow sensor 67.

User selectable triggers perform offset calibrations of sensors 62, 64, 66 that include time from last calibration, temperature from last calibration, carbon dioxide inspired level, oxygen inspired level, and tidal volume imbalance (Ve/Vi) over a series of sample breaths. The tidal volume imbalance provides a parameter that is particularly useful for determining offset calibration. Determined over a reasonable period of breaths (for example, a 7 breath rolling buffer), the total inspired breath volume should correlate to the total expired breath volume. If the values do not correlate, the discrepancy provides indicia that analyzer 32 flow offset has drifted, or that a leak is present in the gas circuit. Also, as part of this feature, the display 36 includes a health meter indication for each trigger.

As shown in FIG. 3, flow leak valve 89 of analyzer 32 is configured to allow analyzer 32 to check for leaks in the gas sampling path and those in the patient flow measurement path. The gas sampling path is from the sensor 34 to the input 57, 59 as shown in FIG. 1. If a leak exists in the gas sampling path and is small, gas waveforms will still be present but will show up with a larger time lag from the patient flow signal. This will result in greater dead-space readings than what are actually present. If the leak in the sampling path is larger, the dead-space becomes very large and the system experiences difficulty attempting: to align the gas concentration with flow and presents a detectable error condition.

To detect small gas sampling leaks, valve 89 is used to close off the sampling line internal to the system immediately after the input to the housing. When closed, the sample pump is used to draw a vacuum to a lower pressure. When this pressure is reached, the pump is turned off and this pressure must be maintained for a desired time. If internal leaks are present, the lower pressure will quickly climb back to ambient pressure providing an indication of an internal leak condition. External leaks are detected as a flow error if either of tubes 44, 46 have a leak. The noticeable affect is an imbalance between inspired and expired volumes depending on location. During a leak check, a user is instructed to connect plugs to a flow sensor and analyzer 32 shuts off valve 72 to either input 57, 59 uses pump 70 to apply positive pressure to the system. As above, positive pressure above ambient must be maintained for a period of time to indicate a no-leak condition.

Analyzer 32 is further configured to automatically calibrate operation of sensors 62, 64, 66 for variable environmental factors including ambient gas concentrations and ambient temperature and humidity. 11. Preferably, oxygen sensor 64 is an electrochemical device. Although such devices generally include an electrical or mechanical temperature compensation feature, such corrections are insufficient to address the parameters associated with respiration monitoring. That is, such corrective measures introduce errors of inherent to the corrective devices. Accordingly, analyzer 32 is constructed to operate in such a way as to address the inherent errors associated with operation of the sensor. Analyzer 32 also adjusts operation as a function of humidity variations associated with operation of the sensors 62, 64, 66.

Figure 21:
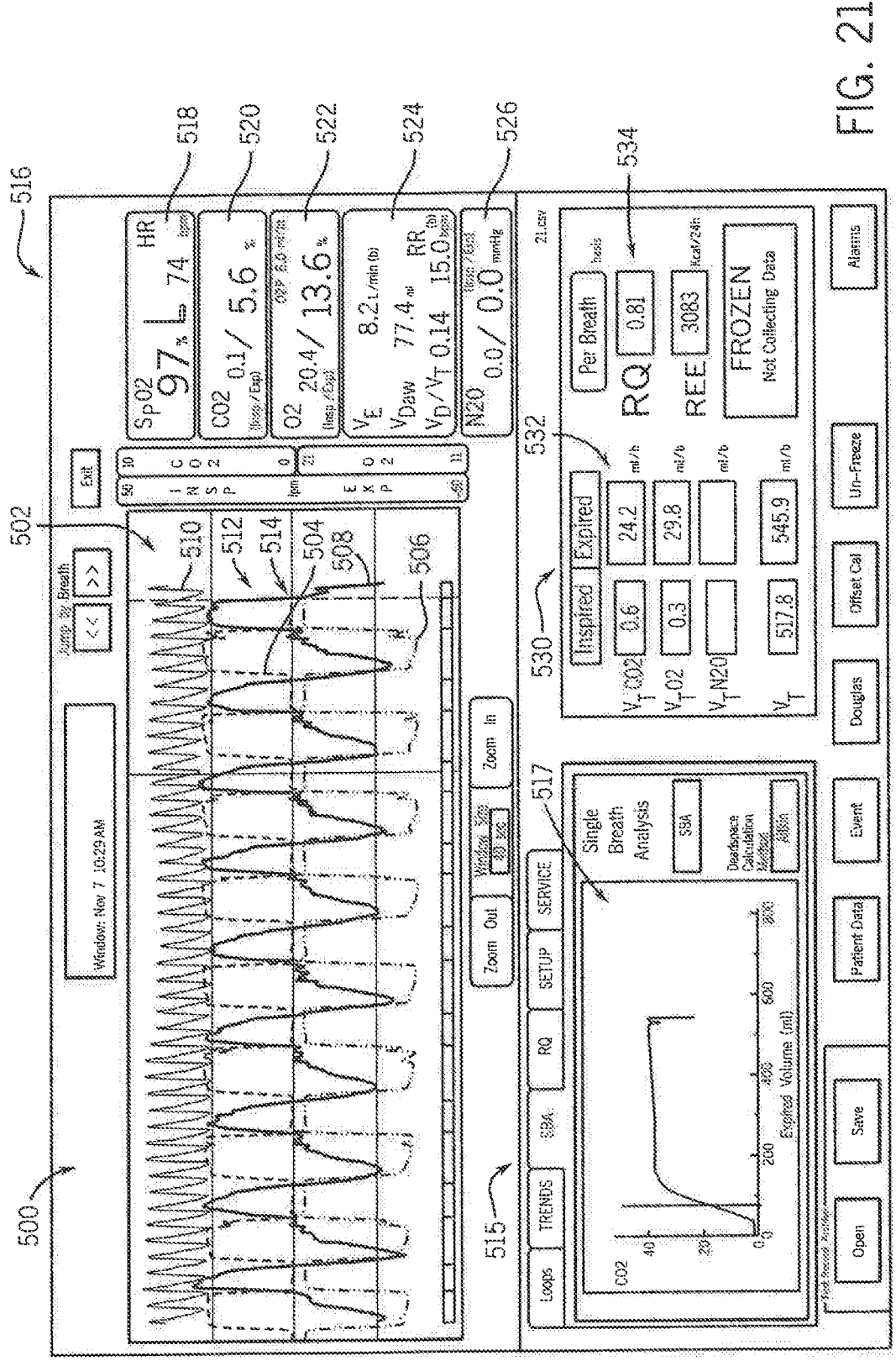
FIG. 21 is an exemplary display of the information acquired and corrected by the respiration gas monitoring system shown in FIG. 2.

FIG. 21 shows an exemplary time-aligned respiration output 500 generated by analyzer 32. Output 500 includes a trend window 502 configured to display a carbon dioxide concentration 504, an oxygen concentration 506, a flow value 508, and a saturated blood oxygen value 510 in a common screen 512 on a common plot 514. As discussed above, each of the respiration cycle concentration values 504, 506, 508, 510 are temporally aligned along the data trend. The carbon dioxide concentration 504 and the oxygen concentration 506 values are generally produced as mirror images of one another such that quick viewing and interpretation of the breath data is achieved. It is further appreciated that the oxygen concentration data could be acquired by scaling the respiration data by a factor such that it correlates to the carbon dioxide concentration value. Alternatively, it is understand that analyzer 32 be configured to monitor the oxygen content deficiency and that this value then be inverted to generally mimic the carbon dioxide concentration value. Both configurations provide a carbon dioxide and oxygen concentration displayed value generally similar to that shown in FIG. 21.

It will further be appreciated that the respiration flow value 508 is also time aligned with the carbon dioxide and oxygen concentrations 504, 506. Output 500 also includes a dead-space trend display 515 configured to allow viewing of both the common plot 514 and a dead-space trace 517 that is utilized to calibrate and align the common trends of the common plot 514. A plurality of value displays 516 are included in output 500 and provide exact values of any of the oxygen saturation value 518, a carbon dioxide concentration 520, an oxygen concentration 522, a flow data 524, and nitrous oxide concentration 526 associated with the data related with any given time along common plot 514. During operation of analyzer 32, any given time of acquisition along common plot 514 can be interrogated for the data associated therewith.

Output 500 also includes a volume and RQ display window 530 configured to display rolling tidal volume data 532 associated with inspired and expired volumes as well as rolling RQ data 534. Analyzer 32 is configured to acquire and determine the oxygen concentration, carbon dioxide concentration, and nitrous oxide concentration on a breath-by-breath basis. Analyzer 32 temporally aligns that acquired data and display and corrects, the data as it is acquired. The compact and time aligned display of the data at output 500 provides a system wherein a technician can quickly ascertain the respiration performance of a patient as well as performance of the analyzer. Understandably, output 500 could be configured to allow various levels of operator interaction with the operation and performance of analyzer 32 as well as the various levels of data, calculation, modification, and calibration performed thereby.

As alluded to above, FIGS. 22-26 relate to the generation and assessment of an extraneous alignment signal that is communicated to the respiration flow associated with a respective sensor 34, 550 and the information associated with which is subsequently acquired and assessed by analyzer 32 to achieve a desired time-domain alignment of the acquired respiration flow and respiration composition data. The extraneous alignment signal protocol has been shown to be particularly advantageous to achieving a desired time alignment of the respiration flow information and respiration composition information when the patient originating information associated with the reverse flow protocol (RFP), such as patient pulsatile effects 304, are too small or fast for utilization of the pulsatile effects to achieve a desired data time alignment accuracy. It is however appreciated that the extraneous alignment signal protocol disclosed below can also be utilized as a verification of the intended alignment when the patient pulsatile effects are sufficient for achieving the desired alignment between the respiration flow information and the respiration composition information.

Figure 22:
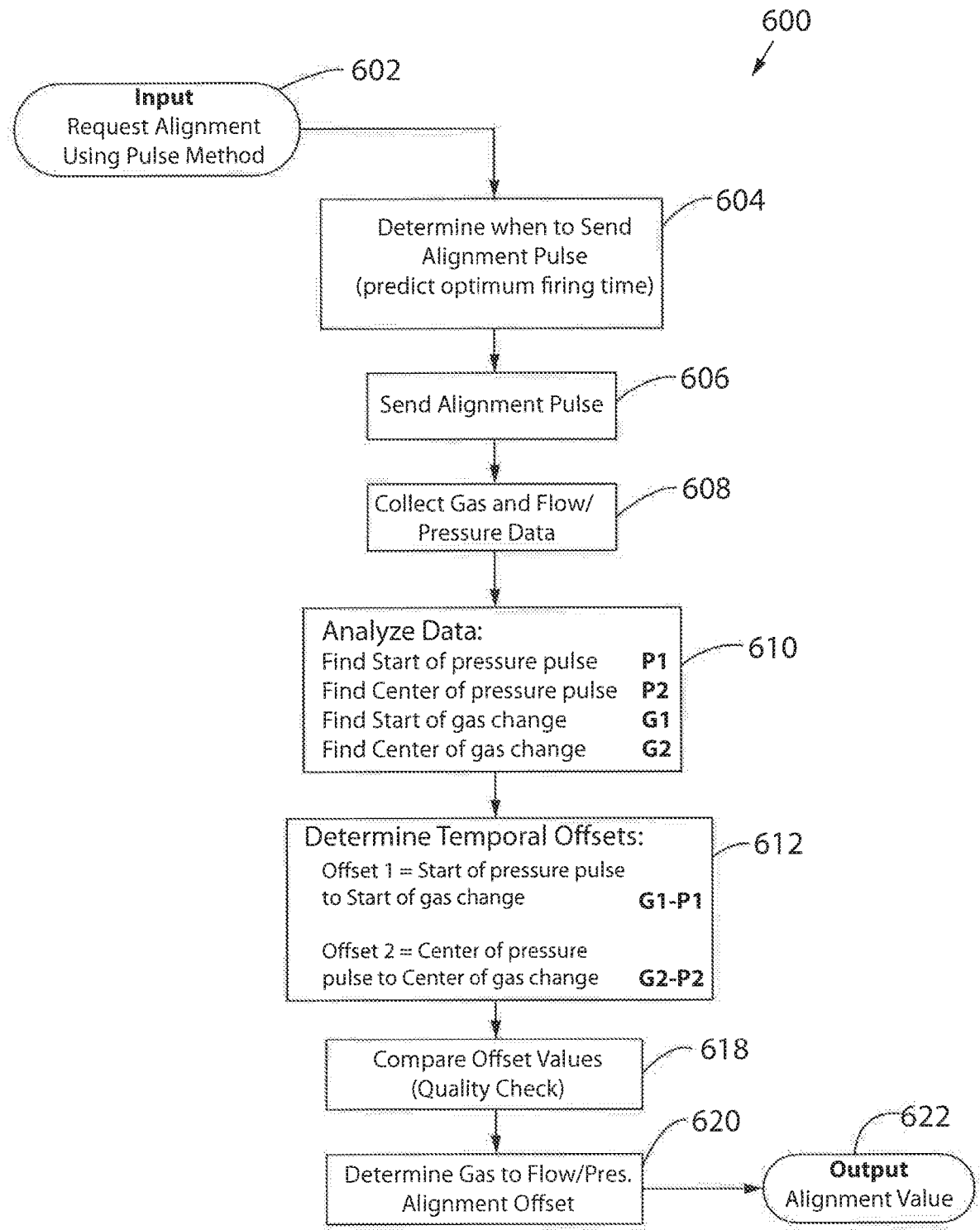
FIG. 22 is a schematic representation of an, alternate respiration flow and composition time alignment protocol that includes an extraneous alignment signal that is communicated to a flow sensor and information associated therewith being subsequently utilized to achieve a flow and composition time alignment offset.

Referring to FIG. 22, extraneous alignment signal protocol 600 associated with monitoring system 30 can include an input 602 associated with analyzer 32 or controller 60 to allow selective operation of the alignment signal protocol 600. For instance, when pulsatile effects 304 are sufficiently represented in the acquired respiration data samples, alignment signal protocol 600 can be disabled. When enabled, alignment signal protocol 600 associated with operation of analyzer 32 first determines when it would be desired to introduce an alignment signal 604 to the respective sensor 34, 550 associated with the respiration flow path. As disclosed below, the alignment signal is preferably introduced to the sensor at a time when the information associated with the alignment signal would be easily assessable from the information associated with respiration performance. The determination of when to introduce the alignment signal 604 is preferable based on previous respiration performance information and/or average values associated a selected number of proceeding breath cycles.

Once determined, an alignment signal is generated 606 by analyzer 32 and communicated to sensor 34, 550. In a preferred embodiment, the alignment signal is a gas signal composed of atmospheric air communicated to sensor 34, 550 via one or more of lumens or tubes 44, 46, 48 associated with sensor 34, 550. It is further appreciated that a dedicated tube and/or port could be provided between sensor 34, 550 and analyzer 32 to effectuate communication of the extraneous flow alignment signal 606 therebetween. Controller 60 and/or pump control 136 associated with analyzer 32 is configured to provide the instruction associated with the desired orientation of one or more of valves 72, 74, 76, 89 and operation of pump 70 to effectuate communication of the alignment signal 606 to sensor 34, 550. After the alignment signal 606 has been communicated to the respective sensor 34, 550, analyzer 32 continues operation of the breath-by-breath assessment of respiration performance via continued collection of a respiration sample and flow/flow pressure data 608. The subsequently acquired respiration sample and flow/pressure information necessarily includes information associated with the alignment signal communicated to respiration flow via sensor 34, 550. Alignment signal 606 has a duration and composition such that the effects of the alignment signal are imperceptible to the patient whose respiration is being monitoring but effects the respiration performance data in a manner wherein the alignment signal can be assessed from the subsequently acquired respiration data.

Figure 23:
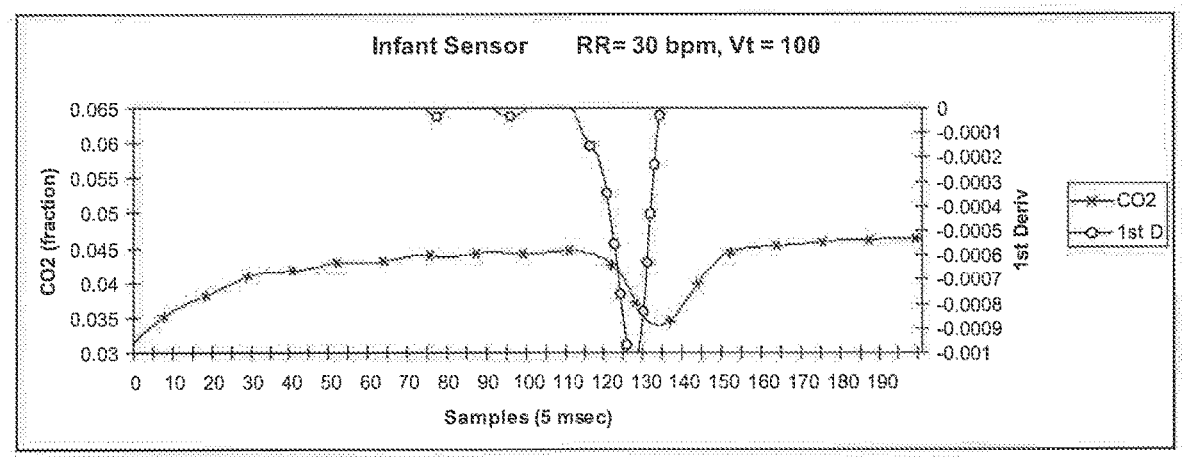
FIGS. 23-26 show various plots associated with the generation of respiration flow and respiration composition data offset values associated with the generating a time domain alignment of the respiration flow and respiration composition data associated with utilization of the extraneous time domain alignment signal.
Figure 24:
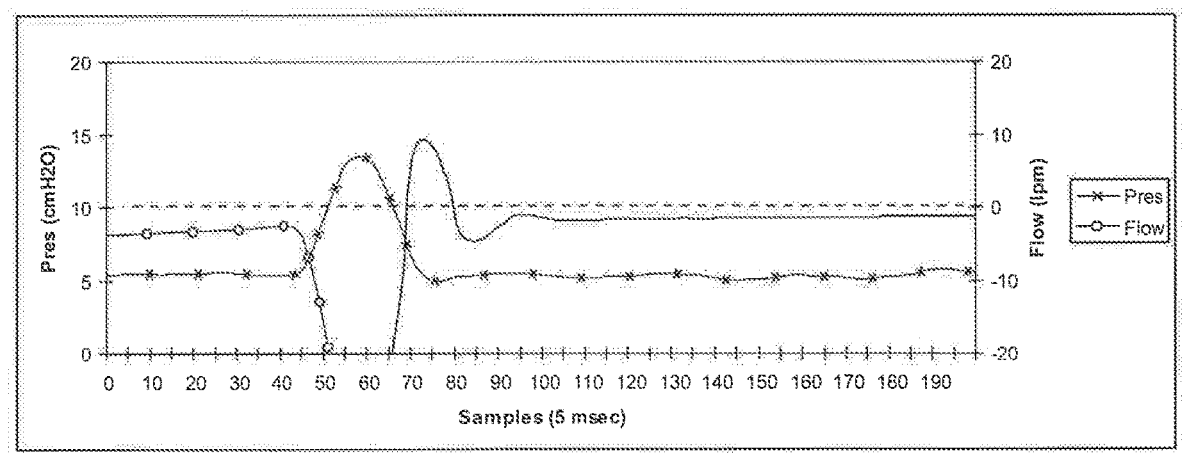
Figure 25:
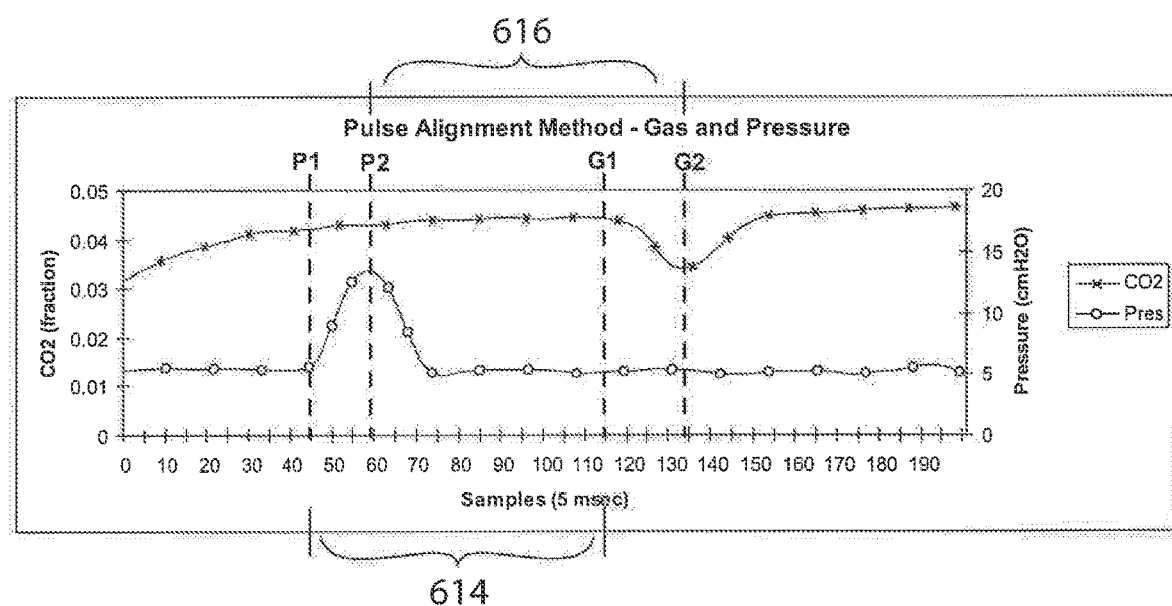

Referring to FIGS. 22-25, upon acquisition of each sidestream-respiration sample and flow signal that includes alignment signal 606, extraneous flow signal alignment protocol 606 assesses the acquired data to determine 610 one or more of the start P1 and center or peak P2 associated with the acquired pressure data and one or more of the start G1 or center G2 associated with the composition with at least one of the constituents of the respiration gas sample. As shown in FIGS. 23-25, various parameters can be utilized to correlate or align the respiration flow data and the respiration composition data to achieve the desired alignment between the flow and composition information. It is further appreciated that the relative changes between one or more of the pressure, relative component concentrations, or alternate pressure or flow and composition information can be utilized to assess the relative or desired offset required to achieve the desired time-wise alignment of the data associated with the respiration flow and respiration composition. That is, information associated with the alignment signal can be assessed from one or more of the relative concentration of a constituent in the respiration flow, such as carbon dioxide relative to a first derivative or rate of change of the carbon dioxide flow as shown in FIG. 23, or a function of the pressure data associated with the flow as shown in FIG. 25, to determine the respective start or appearance of the alignment signal in the acquired data. It is further appreciated that a similar assessment can be provided by a comparison of the flow data relative to the pressure data as shown in FIG. 24. As the flow information is determined from a pressure differential, flow information could be used in place of or in addition to patient flow pressure to determine the desired time-wise alignment of the acquired respiration performance data as both the patient flow and pressure information change concurrently in response to introduction of the alignment signal with the respiration flow stream.

By way of example, as shown graphically in FIG. 25, when the alignment signal 606 is introduced during exhalation associated with a discrete breath cycle, evidence of the alignment signal 606 is reflected in the assessed pressure and/or flow information as a peak or surge relative to the patient respiration associated pressure and/or flow signal indicated by the trend deviation mirrored about vertical axis P2. Similarly, the concentration of carbon dioxide in the exhalation is somewhat constant until introduction of the alignment signal 606 which produces the discontinuity indicated by the trend deviation mirrored about vertical axis G2. Said in another, introduction of alignment signal 606 results in a deviation to the pressure signal that begins at P1, peaks at P2, and the returns to a generally steady state associated with the flow pressure during the discrete portion of the breath cycle. Introduction of the alignment signal 606 is also evidenced in the concentration of carbon dioxide associated with the acquired respiration sample. The alignment signal 606 is represented in the respiration flow sample as a deviation from the somewhat steady state associated with the exhalation sample due to the lower concentration of carbon dioxide associated with the ambient air alignment signal 606 relative to the concentration of carbon dioxide during exhalation. The concentration of carbon dioxide gradually reduces from an initial appearance at G1 until the concentration achieves a minimum at G2, and then recovers to the generally steady state exhalation carbon dioxide concentration. It is appreciated that alignment signal 606 can be provided in a number of forms depending upon where during the respiration cycle the alignment signal is intended to be combined with the respiration flow associated with sensor 34, 550.

Referring back to FIG. 22, once the breath sample that includes the alignment signal has been acquired and the information associated therewith has been assessed, alignment signal protocol 600 determines the value associated with one or more temporal or timewise offsets 612 between the composition, flow, and/or pressure data. Referring to FIGS. 22 and 25, a first offset 614 is determined as the duration between the appearance of the alignment signal in the pressure and/or flow signal P1 and the appearance of the alignment signal in the carbon dioxide concentration signal G1. A second or alternative offset 616 is determined as the duration between the maximum pressure signal P2 and the peak G2 associated with the change to the carbon dioxide concentration signal. It is appreciated that one of offsets 614, 616 could be sufficient to determine and apply a desired offset to achieve the alignment of the respiration flow and respiration concentration data. It is further appreciated to any number of parameters associated with the flow, pressure, and discrete component concentrations could be used from the breath sample that includes at least a portion of the alignment signal to assess the relative alignment between the acquired flow and concentration data.

Figure 26:
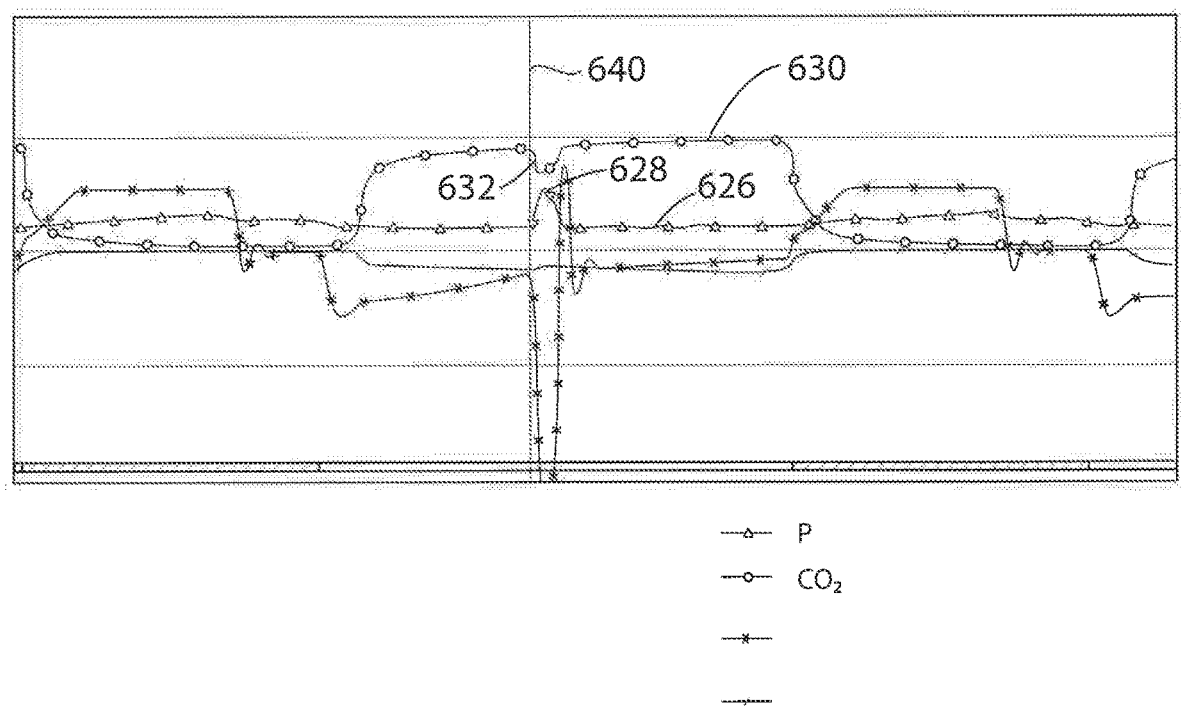

Referring to FIGS. 22, 25, and 26, protocol 606 preferably uses the values associated with first and second offsets 614, 616 to assess the accuracy 618 of the calculated offset and to determine 620 and output a desired offset value 622 to controller 60. Controller 60 utilizes the output offset 622 to generate the time-aligned respiration flow and respiration composition data output 500. It is appreciated that any of averaging and/or weighting of offsets 614, 616 can be implemented to achieve a output offset value 622 that accurately accommodates the discrepancy between the respiration flow and respiration composition data. It is further appreciated that such operation can be conveniently corroborated by conventional experimentational fixturing of system 30 as disclosed further above with respect to the various calibration protocols disclosed herein.

FIG. 26 shows approximately 5 seconds of one of the aligned breath cycles shown in FIG. 21 wherein the temporal or time-wise alignment of the various pressure, flow, and composition trends. As shown in FIG. 26, the pressure trend line 626 includes a deviation 628 associated with the introduction of the alignment signal 606 to a respective sensor 34, 550. The trend line associated with the concentration of carbon dioxide 630 also includes a deviation 632 which, when aligned with deviation 628 as indicated by vertical line 640 allow time-wise alignment of the composition and flow information associated with output 500 on a breath-by-breath basis and in a manner that does not require acquisition or assessment of changes to the respiration performance due to patient physiological events. It is appreciated that, if desired, the deviations associated with the effects of alignment signal 606 can be mathematically corrected by subtraction of the effects of the alignment signal from the flow and composition data displayed to a user. As alluded to above, when the physiologic events occur with sufficient intensity, duration, and repeatability, patient external alignment protocol 600 can be turned off or run as an additional confirmation that system 30 achieves the desired temporal alignment of the acquired respiration flow and respiration composition data. It is further appreciated that alignment signal 606 can be provided in any number of sequences including every breath cycle or an intermittent number of breath cycles, such as one every five breath cycles for instance. Accordingly, analyzer 32 is highly versatile, easy to operate, simple to configure for desired operation, and provides an output that allows for quick diagnosis and analysis of patient condition. Operation of analyzer 32 with the external alignment signal methodology disclosed immediately above further improves the accuracy associated with patient respiration and increases the class of users associated with such systems to include those whose physiologic performance may be insufficient to accommodate accurate assessment of the respiration performance as altered by patient physiologic performance.

Therefore, according to one embodiment of the invention, a side-stream respiration monitoring system includes an analyzer and a controller that is associated with the analyzer. The analyzer is configured to be fluidly connected to a flow sensor that is constructed to be disposed in a respiration flow path. The controller is configured to initiate delivery of an alignment signal generated by the analyzer to the flow sensor during a portion of at least one breath cycle. The controller is further configured to determine a respiration flow value and at least a portion of a composition of the respiration flow on a breath-by-breath basis and temporally associate in a time-domain the determined respiration flow value and the determined portion of the composition associated with the breath-by-breath basis as a function of information associated with the alignment signal delivered to the flow sensor by the analyzer during the portion of the at least one breath cycle.

Another embodiment of the invention useable with one or more of the aspects of the above embodiments discloses a method of monitoring patient respiration performance that includes measuring a patient respiration flow, acquiring a side-stream breath sample, and generating an alignment signal. At least a portion of the alignment signal is acquired with the side-stream breath sample and a flow of the side-stream breath sample and a concentration of oxygen, and a concentration of carbon dioxide in the acquired side-stream breath sample is determined and aligned with one another in a time domain with respect to their occurrence in the acquired side-stream breath sample as a function of information associated with the portion of the alignment signal that is acquired with the side-stream breath sample.

Another embodiment useable with one or more of the above embodiments includes a method of manipulating respiration performance data in a side-stream respiration monitoring system. The method includes introducing an alignment signal to a respiration flow passing through a sensor and determining a flow rate and at least a portion of a composition of a respiration flow passing through the sensor and aligning in a time domain the determined flow rate and the determined portion of the composition of the respiration flow from information attributable to the alignment signal.

It is further understood that specific details described above are not to be interpreted as limiting the scope of the invention, but are provided merely as a basis for teaching one skilled in the art to variously practice the present invention in any appropriate manner. Changes may be made in the details of the various methods and features described herein, without departing from the spirit of the invention

What is claimed is:

1. A side-stream respiration monitoring system, the system comprising:
an analyzer configured to be fluidly connected to a flow sensor that is constructed to be disposed in a respiration flow path; and
a controller associated with the analyzer and configured to:
initiate delivery of a non-patient originated alignment signal generated by a pump of the analyzer and delivered to the flow sensor during a portion of at least one breath cycle when a physiologic event signal cannot be determined from at least one proceeding breath cycle;
determine a respiration flow value and at least a portion of a composition of the respiration flow on a breath-by-breath basis;
temporally associate in a time-domain the respiration flow value and the portion of the composition of the respiration flow associated with the breath-by-breath basis from 1) the determined respiration flow value and the determined portion of the composition of the respiration flow associated with the alignment signal delivered to the flow sensor by the pump of the analyzer during the portion of the at least one breath cycle associated with delivery of the non-patient originated alignment signal when a physiologic event signal cannot be determined from at least one proceeding breath cycle and 2) a respiration flow value and a portion of the composition of the respiration flow associated with a physiologic event when the physiologic event signal is present within a selected number of proceeding breath cycles; and
generate a time-aligned respiration output providing an alignment between the respiration flow value and the portion of the composition from the temporally associated respiration flow value and portion of the composition of the respiration flow.

2. The system of claim 1 wherein the analyzer is configured to deliver the alignment signal to the flow sensor via a lumen associated with at least one of a pressure port and a sample port associated with the flow sensor.

3. The system of claim 2 further comprising another lumen associated with the other of the at least one of the pressure port and the sample port and wherein the alignment signal includes a first portion that is delivered to the pressure port and a second portion that is delivered to the sample port.

4. The system of claim 1 wherein the flow sensor includes a hydrophilic coating associated with a surface of the flow sensor that is exposed to the respiration flow path.

5. The system of claim 1 wherein the controller is configured to determine a time associated with delivery of the alignment signal as a function of at least one of the respiration flow value, an oxygen value detected by an oxygen sensor associated with the analyzer, and a carbon dioxide value detected by a carbon dioxide sensor associated with the analyzer and the time determined by the controller is associated with the portion of the composition of the respiration flow.

6. The system of claim 1 wherein the controller is configured to determine a temporal offset between a change of a pressure signal associated with the respiration flow and a change of a gas signal associated with the composition of the respiration flow, the pressure and gas signals being determined by the analyzer.

7. The system of claim 1 wherein the controller is configured to determine at least one of: a temporal offset value from a start of a change of a pressure signal associated with the respiration flow to a start of a change of a gas signal associated with the composition of the respiration flow; and a temporal offset value from a maximum value of the pressure signal to a minimum value of the gas signal during the portion of the at least one breath cycle associate with delivery of the non-patient originated alignment signal, the pressure and gas signals being determined by the analyzer.

8. The system of claim 7 wherein the controller is configured to generate an offset value from a comparison of the temporal offset value from the start of the change of the pressure signal to the start of the change of the gas signal and the temporal offset value from the maximum value of the pressure signal to the minimum value of the gas signal during the portion of the at least one breath cycle associated with the delivery of the non-patient originated alignment signal.

9. A method of monitoring patient respiration information comprising the steps of:
measuring a patient respiration flow;
acquiring a plurality of side-stream breath samples;

detecting for the presence of a physiologic alignment signal in a selected number of breaths of the plurality of acquired side-stream breath samples;

generating a non-patient originated alignment signal from an analyzer and acquiring at least a portion of the alignment signal with the side-stream breath sample when no physiologic alignment signal is detected in the selected number of breaths of the plurality of acquired side-stream breath samples;

determining a flow of the side-stream breath sample, a concentration of oxygen, and a concentration of carbon dioxide in the acquired side-stream breath sample of the patient respiration flow;

determining an offset associated with the alignment of the determined flow and the determined concentrations of oxygen and carbon dioxide in the time domain from a change of a pressure signal associated with the flow and a change of at least one gas signal associated with the concentrations; and aligning the determined flow with the determined concentrations of oxygen and carbon dioxide in a time domain with respect to their occurrence in the acquired side-stream breath sample of the patient respiration flow as a function of information associated with at least one of the portion of the alignment signal acquired with the portion of the composition of the respiration flow associated with the side-stream breath sample and the physiologic alignment signal for breaths associated with the detection of the presence of the physiologic alignment signal and the non-patient originated alignment signal for breaths when no physiologic alignment signal is detected in the selected number of breaths of the acquired plurality of side-stream breath samples.

10. The method of claim 9 wherein the generation of the alignment signal further comprises introducing a pulse of ambient air to a flow sensor associated with the patient respiration flow.

11. The method of claim 9 further comprising determining a time associated with delivery of the alignment signal from at least one of the respiration flow value, an oxygen value, and a carbon dioxide value associated with a previously acquired side-stream breath sample of the patient respiration flow.

12. The method of claim 9 further comprising determining a first temporal offset value from a start of the change of the pressure signal to a start of the change of the at least one gas signal associated with the concentrations and a second temporal offset value from a maximum value of the pressure signal to a minimum concentration value of the at least one gas signal associated with the concentrations and generating a data offset value from a comparison of the first temporal offset value and the second temporal offset value.

13. The method of claim 9 further comprising generating the alignment signal from a gas source having at least one of a concentration of oxygen and a concentration of carbon dioxide that is different than the concentration of a corresponding one of the concentration of oxygen and the concentration of carbon dioxide associated with a respiration flow in the acquired side-stream breath sample flow associated with the side-stream breath sample.

14. A method of manipulating respiration performance data in a side-stream respiration monitoring system, the method comprising:

detecting for presence of a physiological respiration event signal in at least one breath cycle of a patient;

introducing a non-patient originated alignment signal that is generated by an analyzer to a respiration flow passing through a sensor during a portion of the at least one breath cycle when presence of the physiological respiration event signal is not detected in a selected number of samples that is greater than one of preceding respiration samples;

determining a flow rate and at least a portion of a composition of a respiration flow, including an oxygen concentration and a carbon dioxide concentration, on a breath-by-breath basis, from a flow sample and a pressure signal communicated to the analyzer from the respiration flow passing through the sensor; and temporally associating in a time domain the determined flow rate and the determined portion of the composition of the respiration flow on the breath-by-breath basis as a function of information associated with the physiological respiration event signal for the at least one breath cycle when the physiological respiration event signal is detected and the non-patient originated alignment signal delivered to the sensor by the analyzer during the portion of the at least one breath cycle when the physiological respiration event signal is not detected in the selected number of samples of preceding respiration samples of breath cycles;

generating a time-aligned respiration output providing an alignment between the flow rate and the portion of the composition of the respiration flow from the temporally associated flow rate and portion of the composition of the respiration flow; and determining a temporal offset associated with the alignment of the determined flow rate and concentrations of oxygen and carbon dioxide from the determined at least a portion of the composition of respiration flow on a breath-by-breath basis and the presence of one of the physiologic respiration event signal and the non-patient originated alignment signal in the at least one breath cycle and passing through the sensor and communicated to the analyzer in the time domain from a comparison of at least one of a start of a pressure signal detected by the analyzer from the respiration flow passing through the sensor to a start of a gas composition change and a maximum of a pressure signal to a minimum of a gas composition change from the determined portion of the composition of the respiration flow on the breath-by-breath basis passing through the sensor to the analyzer associated with the breath-by-breath basis.

15. The method of claim 14 further comprising determining an offset associated with alignment of the determined flow and the determined concentrations from at least one of a change of the pressure signal and a change of the composition of the gas signal from the determined portion of the composition of the respiration flow of the breath-by-breath basis passing through the sensor.

16. The method of claim 14 further comprising determining a first temporal offset value associated with the comparison of a start of the pressure signal to a start of the gas composition change and a second temporal offset value associated with the comparison of a maximum of the pressure signal to a minimum of the gas composition change and generating a data offset value from a comparison of the first temporal offset value and the second temporal offset value.

17. The method of claim 14 further comprising displaying a time domain aligned flow rate and the determined portion of the composition of the respiration flow on a common ordinate and abscissa.

18. The method of claim 14 further comprising introducing the alignment signal to a respiration flow passing through a sensor via a pressure port and a breath sample port defined by the sensor.

19. The method of claim 14 wherein the introducing of an alignment signal to a respiration flow passing through a sensor is further defined as communicating an ambient air signal to the respiration flow passing through the sensor.

20. The system of claim 1 wherein the flow sensor comprises a patient end constructed to be disposed in the respiration flow path and a port downstream of the patient end, and wherein the non-patient originated alignment signal generated by the analyzer is delivered to the port.

* * * * *